(12) United States Patent
Wallis

(10) Patent No.: US 6,270,991 B1
(45) Date of Patent: *Aug. 7, 2001

(54) HISTIDINE KINASE

(75) Inventor: Nicola Gail Wallis, Wayne, PA (US)

(73) Assignee: SmithKline Beecham Corporation, Philadelphia, PA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/916,481

(22) Filed: Aug. 22, 1997

Related U.S. Application Data

(63) Continuation-in-part of application No. 08/879,529, filed on Jun. 20, 1997, now abandoned, and a continuation-in-part of application No. 08/879,531, filed on Jun. 20, 1997.

(51) Int. Cl.[7] ............................. C12N 15/00; C07H 12/04
(52) U.S. Cl. .................. 435/69.1; 536/23.7; 435/320.1; 435/325; 435/252.3
(58) Field of Search ................................. 536/23.7, 23.1; 435/6, 69.1, 325, 320.1

(56) References Cited

U.S. PATENT DOCUMENTS 5,656,432 * 8/1997 Claverys et al. .

FOREIGN PATENT DOCUMENTS

| 0 891 984 | 1/1999 | (EP) . |
| WO 98 18930 | 5/1998 | (WO) . |
| WO 98 18931 | 5/1998 | (WO) . |

OTHER PUBLICATIONS

Jazin, E. et al., *Regulatory Peptides*, 47:247–58, 1993.*
Herzog, H. et al., *DNA and Cell Biology*, 12 (6):465–71, 1993.*
Richterich, P., et al., GenBank Submission, Accession No. P33357, "Hypothetical 62.1 KD Protein in MOLR–BGLX Intergenic Region Precursor."
Swanson, et al., "Histidine and Aspartate Phosphorylation: Two–Component Systems and the Limits of Homology", *Trends in Biochemical Sciences*, vol. 19, No. 11, pp. 485–490, Nov. 1, 1994.

* cited by examiner

Primary Examiner—Marianne P. Allen
(74) Attorney, Agent, or Firm—Edward R. Gimmi; Thomas S. Deibert; William T. King

(57) ABSTRACT

The invention provides histidine kinase polypeptides and DNA (RNA) encoding histidine kinase polypeptides and methods for producing such polypeptides by recombinant techniques. Also provided are methods for utilizing histidine kinase polypeptides to screen for antibacterial compounds.

14 Claims, No Drawings

_US 6,270,991 B1_

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 3135 base pairs
      (B) TYPE: nucleic acid
      (C) STRANDEDNESS: double
      (D) TOPOLOGY: linear (xi) SEQUENCE DESCRIPTION: SEQ ID NO:1:

```
GAAAAAGACC CTGTCACCTG AGGAGTATGC AGTTACCCAG GAAAATCAAA CAGAACGAGC      60

TTTCTCAAAC CGTTACTGGG ATAAATTTGA ATCCGGTATC TATGTGGATA TAGCAACTGG     120

GGAACCTCTC TTTTCATCAA AAGACAAATT TGAGTCTGGT TGTGGCTGGC CTAGTTTTAC     180

CCAACCCATC AGTCCAGATG TTGTCACCTA CAAGGAAGAT AAGTCCTACA ATATGACGCG     240

TATGGAAGTG CGGAGCCGAG TAGGAGATTC TCACCTTGGG CATGTCTTTA CGGATGGTCC     300

ACAGGACAAG GGCGGCTTAC GTTACTGTAT CAATAGCCTC TCTATCCGCT TTATTCCCAA     360

AGACCAAATG GAAGAAAAAG GCTACGCTTA TTTACTAGAT TATGTTGATT AATACTCTTC     420

GAAAATCTCT TCAAACCACG TCAGCGTCGC CTTACCGTAT GTAGGGTTAC TGACTCCGTC     480

AGTTTTATCT ACAACCTCAA AGCTATACTT TGAGCTGACT TCGTCAGTTT TATCTACAAC     540

CTCAAAGCGG TACTTTGAGA AACCTGTGGC TATCTTCCTA GTTTACTTTT TGATTTTTAT     600

TGAGTATAAG AGGTCTTTCC TAAGCAGTTA GAGGAGAATT TTGCTATACT GATACTAGTA     660

AGTGGTAAAG GAGCAGAGCA TGACCTACAC AATCTTAATC GTAGAAGATG AATATCTGGT     720

AAGACAAGGT TTGACTAAAC TGGTCAATGT AGCAGCCTAC GATATGGAAA TCATCGGTCA     780

GGCTGAAAAT GGAAGGCAGG CTTGGGAATT GATCCAAAAG CAGGTTCCAG ATATCATTTT     840

AACCGATATC AACATGCCTC ATCTAAATGG CATCCAGTTG GCCAGTCTGG TACGAGAAAC     900

CTATCCTCAG GTTCATTTGG TCTTTTTAAC AGGTTACGAT GATTTTGATT ATGCCTTGTC     960

TGCTGTCAAA CTAGGTGTGG ACGACTACCT GCTCAAACCC TTTTCTCGTC AGGATATTGA    1020

GGAAATGTTG GGGAAAATCA AACAAAAACT AGACAAGGAA GAGAAAGAAG AGCAGTTACA    1080

AGATTTATTG ACTAATAGGT TTGAAGGAAA CATGGCCCAG AAAATCCAGT CTCATCGGCC    1140

TGATAGCCAA TTTAGTTTAA AGTCTTTAGC CAGTGACTTA GGTTTTAGTC CGACCTATCT    1200

GAGTTCCTTG ATTAAGAAAG AGTTGGGCTT GCCTTTTCAG GATTATCTAG TGAGAGAACG    1260
```

-continued

```
TGTTAAACAA GCCAAGCTCT TGCTTTTAAC TACAGATCTG AAGATTTATG AGATCGCAGA    1320

GAAGGTTGGT TTTGAAGATA TGAACTATTT TACCCAACGT TTTAAGCAGA TTGCAGGTGT    1380

GACACCTCGT CAGTTTAAGA AGGGAGAAGA CCGATGAAGC GTTCTTCTCT TTTAGTTAGA    1440

ATGGTTATTT CCATCTTTCT GGTCTTTCTC ATTCTCCTAG CTCTGGTTGG AACTTTCTAC    1500

TATCAATCAA GTTCTTCAGC CATTGAGGCC ACCATTGAGG GCAACAGCCA AACGACCATC    1560

AGCCAGACTA GCCACTTTAT TCAGTCTTAT ATCAAAAAAC TAGAAACCAC TTCGACCGGT    1620

TTGACCCAGC AGACGGATGT TCTGGCCTAT GCTGAGAATC CCAGTCAAGA CAAGGTCGAG    1680

GGAATCCGAG ATTTGTTTTT GACCATCTTG AAGTCAGATA AGGACTTGAA ACTGTTGTG    1740

CTGGTGACCA AATCTGGTCA GGTCATTTCT ACAGATGACA GTGTGCAGAT GAAAACTTCC    1800

TCTGATATGA TGGCTGAGGA TTGGTACCAA AAGGCCATTC ATCAGGGAGT GATGCCTGTT    1860

TTGACTCCAG CTCGTAAATC AGATAGTCAG TGGGTCATTT CTGTCACTCA AGAACTTGTT    1920

GATGCAAAGG GAGCCAATCT TGGTGTGCTT CGTTTGGATA TTTCTTATGA AACTCTGGAA    1980

GCCTATCTCA ATCAACTCCA GTTGGGGCAG CAGGGCTTTG CCTTCATTAT CAATGAAAAC    2040

CATGAATTTG TCTACCATCC TCAACACACA GTTTATAGTT CGTCTAGCAA ATGGAGGCT     2100

ATGAAACCCT ACATCGAGAC AGGTCAGGGT TATACTCCTG GTCACAAATC CTACGTCAGT    2160

CAAGAGAAGA TTGCAGGAAC TGATTGGACG GTACTTGGCG TGTCATCATT GGAAAAGTTA    2220

GACCAGGTTC GGAGTCAGCT CTTGTGGACC TTGCTTGGGG CCAGTGTCAC ATCTCTTCTT    2280

GTCTGTCTCT GCTTAGTGTG GTTCAGTCTT AAACGCTGGA TTGCTCCTTT GAAGGATTTG    2340

AGAGAAACCA TGTTGGAAAT TGCTTCTGGT GCTCAAAATC TTCGTGCCAA GGAAGTTGGT    2400

GCCTATGAAC TGAGAGAAGT AACTCGCCAA TTTAATGCCA TGTTGGATCA GATTGATCAG    2460

TTGATGGTAG CTATTCGTAG CCAGGGAGAA ACGACCCGTC AGTACCAACT TCAAGCCCTT    2520

TCGAGCCAGA TTAATCCACA TTTCCTCTAT AACACTTTGG ACACCATCAT CTGGATGGCT    2580

GAATTTCATG ATAGTCAGCG AGTGGTGCAG GTGACCAAGT CCTTGGCAAC CTATTTCCGC    2640

TTGGCACTCA ATCAAGGCAA AGACTTGATT TGTCTCTCTG ACGAAATCAA TCATGTCCGC    2700

CAGTATCTCT TTATCCAGAA ACAACGCTAT GGAGATAAGC TGGAATACGA AATTAATGAA    2760

AATGTTGCCT TTGATAATTT AGTCTTACCC AAGCTGGTCC TACAACCCCT TGTAGAAAAT    2820

GCTCTTTACC ATGGCATTAA GGAAAAGGAA GGTCAGGGCC ATATTAAACT TTCTGTCCAG    2880

AAACAGGATT CGGGATTGGT CATCCGTATT GAGGATGATG GCGTTGGCTT CCAAAATGCT    2940

GGTGATAGTA GTCAAAGTCA ACTCAAACGT GGGGGAGTTG GTCTTCAAAA TGTCGATCAA    3000

CGGCTCAAAC TTCATTTTGG AGCCAATTAC CAGATGAAGA TTGATTCTAC ACCCCAAAAA    3060

GGGACGAAAG TTGAAATATA TATAAATACA GTAGAAACTA GATAACTCCC AGTCAATTCT    3120

GGGAGTCTTA TGCGT                                                     3135
```

(2) INFORMATION FOR SEQ ID NO:2:

(i) SEQUENCE CHARACTERISTICS:
        (A) LENGTH: 554 amino acids
        (B) TYPE: amino acid
        (C) STRANDEDNESS: single
        (D) TOPOLOGY: linear (xi) SEQUENCE DESCRIPTION: SEQ ID NO:2:

```
Met Val Ile Ser Ile Phe Leu Val Phe Leu Ile Leu Leu Ala Leu Val
 1               5                  10                  15
```

```
Gly Thr Phe Tyr Tyr Gln Ser Ser Ser Ala Ile Glu Ala Thr Ile
                20              25              30

Glu Gly Asn Ser Gln Thr Thr Ile Ser Gln Thr Ser His Phe Ile Gln
            35                  40                  45

Ser Tyr Ile Lys Lys Leu Glu Thr Thr Ser Thr Gly Leu Thr Gln Gln
        50                  55                  60

Thr Asp Val Leu Ala Tyr Ala Glu Asn Pro Ser Gln Asp Lys Val Glu
65                  70                  75                  80

Gly Ile Arg Asp Leu Phe Leu Thr Ile Leu Lys Ser Asp Lys Asp Leu
                85                  90                  95

Lys Thr Val Val Leu Val Thr Lys Ser Gly Gln Val Ile Ser Thr Asp
            100                 105                 110

Asp Ser Val Gln Met Lys Thr Ser Ser Asp Met Met Ala Glu Asp Trp
            115                 120                 125

Tyr Gln Lys Ala Ile His Gln Gly Val Met Pro Val Leu Thr Pro Ala
            130                 135                 140

Arg Lys Ser Asp Ser Gln Trp Val Ile Ser Val Thr Gln Glu Leu Val
145                 150                 155                 160

Asp Ala Lys Gly Ala Asn Leu Gly Val Leu Arg Leu Asp Ile Ser Tyr
                165                 170                 175

Glu Thr Leu Glu Ala Tyr Leu Asn Gln Leu Gln Leu Gly Gln Gln Gly
            180                 185                 190

Phe Ala Phe Ile Ile Asn Glu Asn His Glu Phe Val Tyr His Pro Gln
            195                 200                 205

His Thr Val Tyr Ser Ser Ser Lys Met Glu Ala Met Lys Pro Tyr
            210                 215                 220

Ile Glu Thr Gly Gln Gly Tyr Thr Pro Gly His Lys Ser Tyr Val Ser
225                 230                 235                 240

Gln Glu Lys Ile Ala Gly Thr Asp Trp Thr Val Leu Gly Val Ser Ser
                245                 250                 255

Leu Glu Lys Leu Asp Gln Val Arg Ser Gln Leu Leu Trp Thr Leu Leu
            260                 265                 270

Gly Ala Ser Val Thr Ser Leu Leu Val Cys Leu Cys Leu Val Trp Phe
            275                 280                 285

Ser Leu Lys Arg Trp Ile Ala Pro Leu Lys Asp Leu Arg Glu Thr Met
            290                 295                 300

Leu Glu Ile Ala Ser Gly Ala Gln Asn Leu Arg Ala Lys Glu Val Gly
305                 310                 315                 320

Ala Tyr Glu Leu Arg Glu Val Thr Arg Gln Phe Asn Ala Met Leu Asp
                325                 330                 335

Gln Ile Asp Gln Leu Met Val Ala Ile Arg Ser Gln Gly Glu Thr Thr
            340                 345                 350

Arg Gln Tyr Gln Leu Gln Ala Leu Ser Ser Gln Ile Asn Pro His Phe
            355                 360                 365

Leu Tyr Asn Thr Leu Asp Thr Ile Ile Trp Met Ala Glu Phe His Asp
            370                 375                 380

Ser Gln Arg Val Val Gln Val Thr Lys Ser Leu Ala Thr Tyr Phe Arg
385                 390                 395                 400

Leu Ala Leu Asn Gln Gly Lys Asp Leu Ile Cys Leu Ser Asp Glu Ile
                405                 410                 415

Asn His Val Arg Gln Tyr Leu Phe Ile Gln Lys Gln Arg Tyr Gly Asp
            420                 425                 430

Lys Leu Glu Tyr Glu Ile Asn Glu Asn Val Ala Phe Asp Asn Leu Val
```

-continued

```
                435                 440                 445
Leu Pro Lys Leu Val Leu Gln Pro Leu Val Glu Asn Ala Leu Tyr His
    450                 455                 460

Gly Ile Lys Glu Lys Glu Gly Gln Gly His Ile Lys Leu Ser Val Gln
465                 470                 475                 480

Lys Gln Asp Ser Gly Leu Val Ile Arg Ile Glu Asp Gly Val Gly
                485                 490                 495

Phe Gln Asn Ala Gly Asp Ser Gln Ser Gln Leu Lys Arg Gly Gly
                500                 505                 510

Val Gly Leu Gln Asn Val Asp Gln Arg Leu Lys Leu His Phe Gly Ala
        515                 520                 525

Asn Tyr Gln Met Lys Ile Asp Ser Thr Pro Gln Lys Gly Thr Lys Val
    530                 535                 540

Glu Ile Tyr Ile Asn Thr Val Glu Thr Arg
545                 550
```

(2) INFORMATION FOR SEQ ID NO:3:

(i) SEQUENCE CHARACTERISTICS:
       (A) LENGTH: 563 amino acids
       (B) TYPE: amino acid
       (C) STRANDEDNESS: single
       (D) TOPOLOGY: linear (xi) SEQUENCE DESCRIPTION: SEQ ID NO:3:

```
Met Lys Arg Ser Ser Leu Leu Val Arg Met Val Ile Ser Ile Phe Leu
1               5                   10                  15

Val Phe Leu Ile Leu Leu Ala Leu Val Gly Thr Phe Tyr Tyr Gln Ser
            20                  25                  30

Ser Ser Ser Ala Ile Glu Ala Thr Ile Glu Gly Asn Ser Gln Thr Thr
        35                  40                  45

Ile Ser Gln Thr Ser His Phe Ile Gln Ser Tyr Ile Lys Lys Leu Glu
    50                  55                  60

Thr Thr Ser Thr Gly Leu Thr Gln Gln Thr Asp Val Leu Ala Tyr Ala
65              70                  75                  80

Glu Asn Pro Ser Gln Asp Lys Val Glu Gly Ile Arg Asp Leu Phe Leu
            85                  90                  95

Thr Ile Leu Lys Ser Asp Lys Asp Leu Lys Thr Val Val Leu Val Thr
            100                 105                 110

Lys Ser Gly Gln Val Ile Ser Thr Asp Asp Ser Val Gln Met Lys Thr
        115                 120                 125

Ser Ser Asp Met Met Ala Glu Asp Trp Tyr Gln Lys Ala Ile His Gln
130                 135                 140

Gly Val Met Pro Val Leu Thr Pro Ala Arg Lys Ser Asp Ser Gln Trp
145                 150                 155                 160

Val Ile Ser Val Thr Gln Glu Leu Val Asp Ala Lys Gly Ala Asn Leu
                165                 170                 175

Gly Val Leu Arg Leu Asp Ile Ser Tyr Glu Thr Leu Glu Ala Tyr Leu
            180                 185                 190

Asn Gln Leu Gln Leu Gly Gln Gln Gly Phe Ala Phe Ile Ile Asn Glu
        195                 200                 205

Asn His Glu Phe Val Tyr His Pro Gln His Thr Val Tyr Ser Ser Ser
    210                 215                 220

Ser Lys Met Glu Ala Met Lys Pro Tyr Ile Glu Thr Gly Gln Gly Tyr
225                 230                 235                 240
```

```
Thr Pro Gly His Lys Ser Tyr Val Ser Gln Glu Lys Ile Ala Gly Thr
                245                 250                 255

Asp Trp Thr Val Leu Gly Val Ser Ser Leu Glu Lys Leu Asp Gln Val
            260                 265                 270

Arg Ser Gln Leu Leu Trp Thr Leu Leu Gly Ala Ser Val Thr Ser Leu
        275                 280                 285

Leu Val Cys Leu Cys Leu Val Trp Phe Ser Leu Lys Arg Trp Ile Ala
    290                 295                 300

Pro Leu Lys Asp Leu Arg Glu Thr Met Leu Glu Ile Ala Ser Gly Ala
305                 310                 315                 320

Gln Asn Leu Arg Ala Lys Glu Val Gly Ala Tyr Glu Leu Arg Glu Val
                325                 330                 335

Thr Arg Gln Phe Asn Ala Met Leu Asp Gln Ile Asp Gln Leu Met Val
            340                 345                 350

Ala Ile Arg Ser Gln Gly Glu Thr Thr Arg Gln Tyr Gln Leu Gln Ala
        355                 360                 365

Leu Ser Ser Gln Ile Asn Pro His Phe Leu Tyr Asn Thr Leu Asp Thr
    370                 375                 380

Ile Ile Trp Met Ala Glu Phe His Asp Ser Gln Arg Val Val Gln Val
385                 390                 395                 400

Thr Lys Ser Leu Ala Thr Tyr Phe Arg Leu Ala Leu Asn Gln Gly Lys
                405                 410                 415

Asp Leu Ile Cys Leu Ser Asp Glu Ile Asn His Val Arg Gln Tyr Leu
            420                 425                 430

Phe Ile Gln Lys Gln Arg Tyr Gly Asp Lys Leu Glu Tyr Glu Ile Asn
        435                 440                 445

Glu Asn Val Ala Phe Asp Asn Leu Val Leu Pro Lys Leu Val Leu Gln
    450                 455                 460

Pro Leu Val Glu Asn Ala Leu Tyr His Gly Ile Lys Glu Lys Glu Gly
465                 470                 475                 480

Gln Gly His Ile Lys Leu Ser Val Gln Lys Gln Asp Ser Gly Leu Val
                485                 490                 495

Ile Arg Ile Glu Asp Asp Gly Val Gly Phe Gln Asn Ala Gly Asp Ser
            500                 505                 510

Ser Gln Ser Gln Leu Lys Arg Gly Gly Val Gly Leu Gln Asn Val Asp
        515                 520                 525

Gln Arg Leu Lys Leu His Phe Gly Ala Asn Tyr Gln Met Lys Ile Asp
    530                 535                 540

Ser Thr Pro Gln Lys Gly Thr Lys Val Glu Ile Tyr Ile Asn Thr Val
545                 550                 555                 560

Glu Thr Arg (2) INFORMATION FOR SEQ ID NO:4:

(i) SEQUENCE CHARACTERISTICS:
        (A) LENGTH: 3135 base pairs
        (B) TYPE: nucleic acid
        (C) STRANDEDNESS: double
        (D) TOPOLOGY: linear (xi) SEQUENCE DESCRIPTION: SEQ ID NO:4:

GAAAAGACC CTGTCACCTG AGGAGTATGC AGTTACCCAG GAAAATCAAA CAGAACGAGC     60

TTTCTCAAAC CGTTACTGGG ATAAATTTGA ATCCGGTATC TATGTGGATA TAGCAACTGG    120

GGAACCTCTC TTTTCATCAA AGACAAATT TGAGTCTGGT TGTGGCTGGC CTAGTTTTAC    180
```

```
                                                          -continued

CCAACCCATC AGTCCAGATG TTGTCACCTA CAAGGAAGAT AAGTCCTACA ATATGACGCG       240

TATGGAAGTG CGGAGCCGAG TAGGAGATTC TCACCTTGGG CATGTCTTTA CGGATGGTCC       300

ACAGGACAAG GGCGGCTTAC GTTACTGTAT CAATAGCCTC TCTATCCGCT TTATTCCCAA       360

AGACCAAATG GAAGAAAAAG GCTACGCTTA TTTACTAGAT TATGTTGATT AATACTCTTC       420

GAAAATCTCT TCAAACCACG TCAGCGTCGC CTTACCGTAT GTAGGGTTAC TGACTCCGTC       480

AGTTTTATCT ACAACCTCAA AGCTATACTT TGAGCTGACT TCGTCAGTTT TATCTACAAC       540

CTCAAAGCGG TACTTTGAGA AACCTGTGGC TATCTTCCTA GTTTACTTTT TGATTTTTAT       600

TGAGTATAAG AGGTCTTTCC TAAGCAGTTA GAGGAGAATT TTGCTATACT GATACTAGTA       660

AGTGGTAAAG GAGCAGAGCA TGACCTACAC AATCTTAATC GTAGAAGATG AATATCTGGT       720

AAGACAAGGT TTGACTAAAC TGGTCAATGT AGCAGCCTAC GATATGGAAA TCATCGGTCA       780

GGCTGAAAAT GGAAGGCAGG CTTGGGAATT GATCCAAAAG CAGGTTCCAG ATATCATTTT       840

AACCGATATC AACATGCCTC ATCTAAATGG CATCCAGTTG GCCAGTCTGG TACGAGAAAC       900

CTATCCTCAG GTTCATTTGG TCTTTTTAAC AGGTTACGAT GATTTTGATT ATGCCTTGTC       960

TGCTGTCAAA CTAGGTGTGG ACGACTACCT GCTCAAACCC TTTTCTCGTC AGGATATTGA      1020

GGAAATGTTG GGGAAAATCA ACAAAAACT AGACAAGGAA GAGAAAGAAG AGCAGTTACA       1080

AGATTTATTG ACTAATAGGT TTGAAGGAAA CATGGCCCAG AAAATCCAGT CTCATCTGGC      1140

TGATAGCCAA TTTAGTTTAA AGTCTTTAGC CAGTGACTTA GGTTTTAGTC CGACCTATCT      1200

GAGTTCCTTG ATTAAGAAAG AGTTGGGCTT GCCTTTTCAG GATTATCTAG TGAGAGAACG      1260

TGTTAAACAA GCCAAGCTCT TGCTTTTAAC TACAGATCTG AAGATTTATG AGATCGCAGA      1320

GAAGGTTGGT TTTGAAGATA TGAACTATTT TACCCAACGT TTTAAGCAGA TTGCAGGTGT      1380

GACACCTCGT CAGTTTAAGA AGGGAGAAGA CCGATGAAGC GTTCTTCTCT TTTAGTTAGA      1440

ATGGTTATTT CCATCTTTCT GGTCTTTCTC ATTCTCCTAG CTCTGGTTGG AACTTTCTAC      1500

TATCAATCAA GTTCTTCAGC CATTGAGGCC ACCATTGAGG GCAACAGCCA AACGACCATC      1560

AGCCAGACTA GCCACTTTAT TCAGTCTTAT ATCAAAAAAC TAGAAACCAC TTCGACCGGT      1620

TTGACCCAGC AGACGGATGT TCTGGCCTAT GCTGAGAATC CCAGTCAAGA CAAGGTCGAG      1680

GGAATCCGAG ATTTGTTTTT GACCATCTTG AAGTCAGATA AGGACTTGAA AACTGTTGTG      1740

CTGGTGACCA AATCTGGTCA GGTCATTTCT ACAGATGACA GTGTGCAGAT GAAAACTTCC      1800

TCTGATATGA TGGCTGAGGA TTGGTACCAA AAGGCCATTC ATCAGGGAGT GATGCCTGTT      1860

TTGACTCCAG CTCGTAAATC AGATAGTCAG TGGGTCATTT CTGTCACTCA AGAACTTGTT      1920

GATGCAAAGG GAGCCAATCT TGGTGTGCTT CGTTTGGATA TTTCTTATGA AACTCTGGAA      1980

GCCTATCTCA ATCAACTCCA GTTGGGGCAG CAGGGCTTTG CCTTCATTAT CAATGAAAAC      2040

CATGAATTTG TCTACCATCC TCAACACACA GTTTATAGTT CGTCTAGCAA AATGGAGGCT      2100

ATGAAACCCT ACATCGAGAC AGGTCAGGGT TATACTCCTG GTCACAAATC CTACGTCAGT      2160

CAAGAGAAGA TTGCAGGAAC TGATTGGACG GTACTTGGCG TGTCATCATT GGAAAAGTTA      2220

GACCAGGTTC GGAGTCAGCT CTTGTGGACC TTGCTTGGGG CCAGTGTCAC ATCTCTTCTT      2280

GTCTGTCTCT GCTTAGTGTG GTTCAGTCTT AAACGCTGGA TTGCTCCTTT GAAGGATTTG      2340

AGAGAAACCA TGTTGGAAAT GCTTCTGGT GCTCAAAATC TTCGTGCCAA GGAAGTTGGT       2400

GCCTATGAAC TGAGAGAAGT AACTCGCCAA TTTAATGCCA TGTTGGATCA GATTGATCAG      2460

TTGATGGTAG CTATTCGTAG CCAGGGAGAA ACGACCCGTC AGTACCAACT TCAAGCCCTT      2520

TCGAGCCAGA TTAATCCACA TTTCCTCTAT AACACTTTGG ACACCATCAT CTGGATGGCT      2580
```

```
GAATTTCATG ATAGTCAGCG AGTGGTGCAG GTGACCAAGT CCTTGGCAAC CTATTTCCGC    2640

TTGGCACTCA ATCAAGGCAA AGACTTGATT TGTCTCTCTG ACGAAATCAA TCATGTCCGC    2700

CAGTATCTCT TTATCCAGAA ACAACGCTAT GGAGATAAGC TGGAATACGA AATTAATGAA    2760

AATGTTGCCT TTGATAATTT AGTCTTACCC AAGCTGGTCC TACAACCCCT TGTAGAAAAT    2820

GCTCTTTACC ATGGCATTAA GGAAAAGGAA GGTCAGGGCC ATATTAAACT TTCTGTCCAG    2880

AAACAGGATT CGGGATTGGT CATCCGTATT GAGGATGATG GCGTTGGCTT CCAAAATGCT    2940

GGTGATAGTA GTCAAAGTCA ACTCAAACGT GGGGGAGTTG GTCTTCAAAA TGTCGATCAA    3000

CGGCTCAAAC TTCATTTTGG AGCCAATTAC CAGATGAAGA TTGATTCTAC ACCCCAAAAA    3060

GGGACGAAAG TTGAAATATA TATAAATACA GTAGAAACTA GATAACTCCC AGTCAATTCT    3120

GGGAGTCTTA TGCGT                                                    3135
```

(2) INFORMATION FOR SEQ ID NO:5:

(i) SEQUENCE CHARACTERISTICS:
        (A) LENGTH: 245 amino acids
        (B) TYPE: amino acid
        (C) STRANDEDNESS: single
        (D) TOPOLOGY: linear (xi) SEQUENCE DESCRIPTION: SEQ ID NO:5:

```
Met Thr Tyr Thr Ile Leu Ile Val Glu Asp Glu Tyr Leu Val Arg Gln
 1               5                  10                  15

Gly Leu Thr Lys Leu Val Asn Val Ala Ala Tyr Asp Met Glu Ile Ile
                20                  25                  30

Gly Gln Ala Glu Asn Gly Arg Gln Ala Trp Glu Leu Ile Gln Lys Gln
            35                  40                  45

Val Pro Asp Ile Ile Leu Thr Asp Ile Asn Met Pro His Leu Asn Gly
        50                  55                  60

Ile Gln Leu Ala Ser Leu Val Arg Glu Thr Tyr Pro Gln Val His Leu
65                  70                  75                  80

Val Phe Leu Thr Gly Tyr Asp Asp Phe Asp Tyr Ala Leu Ser Ala Val
                85                  90                  95

Lys Leu Gly Val Asp Asp Tyr Leu Leu Lys Pro Phe Ser Arg Gln Asp
            100                 105                 110

Ile Glu Glu Met Leu Gly Lys Ile Lys Gln Lys Leu Asp Lys Glu Glu
        115                 120                 125

Lys Glu Glu Gln Leu Gln Asp Leu Leu Thr Asn Arg Phe Glu Gly Asn
    130                 135                 140

Met Ala Gln Lys Ile Gln Ser His Leu Ala Asp Ser Gln Phe Ser Leu
145                 150                 155                 160

Lys Ser Leu Ala Ser Asp Leu Gly Phe Ser Pro Thr Tyr Leu Ser Ser
                165                 170                 175

Leu Ile Lys Lys Glu Leu Gly Leu Pro Phe Gln Asp Tyr Leu Val Arg
            180                 185                 190

Glu Arg Val Lys Gln Ala Lys Leu Leu Leu Thr Asp Leu Lys
        195                 200                 205

Ile Tyr Glu Ile Ala Glu Lys Val Gly Phe Glu Asp Met Asn Tyr Phe
    210                 215                 220

Thr Gln Arg Phe Lys Gln Ile Ala Gly Val Thr Pro Arg Gln Phe Lys
225                 230                 235                 240

Lys Gly Glu Asp Arg
                245
```

```
(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:6:

ATGGTTATTT CCATCTTTCT GGTC                                          24

(2) INFORMATION FOR SEQ ID NO:7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:7:

TCTAGTTTCT ACTGTATTTA TATAT                                         25
```

HISTIDINE KINASE

RELATED APPLICATIONS

This application is a Continuation-in-part of U.S. Pat. application Ser. No. 08/879,529, filed on Jun. 20, 1997 and abandoned and a continuation-in-part of U.S. Pat. application Ser. No. 08/879,531, filed on Jun. 20, 1997.

FIELD OF THE INVENTION

This invention relates to newly identified polynucleotides and polypeptides, and their production and uses, as well as their variants, agonists and antagonists, and their uses. In particular, in these and in other regards, the invention relates to novel polynucleotides and polypeptides of the histidine kinase family, hereinafter referred to as "histidine kinase".

BACKGROUND OF THE INVENTION

The Streptococci make up a medically important genera of microbes known to cause several types of disease in humans, including, for example, otitis media, conjunctivitis, pneumonia, bacteremia, meningitis, sinusitis, pleural empyema and endocarditis, and most particularly meningitis, such as for example infection of cerebrospimal fluid. Since its isolation more than 100 years ago, _Streptococcus pneumoniae_ has been one of the more intensively studied microbes. For example, much of our early understanding that DNA is, in fact, the genetic material was predicated on the work of Griffith and of Avery, Macleod and McCarty using this microbe. Despite the vast amount of research with _S. pneumoniae_, many questions concerning the virulence of this microbe remain. It is particularly preferred to employ Streptococcal genes and gene products as targets for the development of antibiotics.

The frequency of _Streptococcus pneumoniae_ infections has risen dramatically in the past 20 years. This has been attributed to the emergence of multiply antibiotic resistant strains and an increasing population of people with weakened immune systems. It is no longer uncommon to isolate _Streptococcus pneumoniae_ stains which are resistant to some or all of the standard antibiotics. This has created a demand for both new anti-microbial agents and diagnostic tests for this organism.

While certain Streptococcal factors associated with pathogenicity have been identified, e.g., capsule polysaccharides, peptidoglycans, pneumolysins, PspA Complement factor H binding component, autolysin, neuraminidase, peptide permeases, hydrogen peroxide, IgA1 protease, the list is certainly not complete. Further very little is known concemrig the temporal expression of such genes during infection and disease progression in a mammalian host. Discovering the sets of genes the bacterium is likely to be expressing at the different stages of infection, particularly when an infection is established, provides critical information for the screening and characterization of novel antibacterials which can interrupt pathogenesis. In addition to providing a fuller understanding of known proteins, such an approach will identify previously unrecognised targets.

Many two component signal transduction systems (TCSTS) have been identified in bacteria (Stock, J. B., Ninfa, A. J. & Stock, A. M.(1989) Microbiol. Rev. 53, 450–490). These are involved in the bacterium's ability to monitor its surroundings and adapt to changes in its environment. Several of these bacterial TCSTS are involved in virulence and bacterial pathogenesis within the host.

Histidine kinases are components of the TCSTS which autophosphorylate a histidine residue. The phosphate group is then transferred to the cognate reponse regulator. The Histidine kinases have five short conserved amino acid sequences (Stock, J. B., Ni A. J. & Stock, A. M. (1989) Microbiol. Rev. 53, 450–490, Swanson, R. V., Alex, L. A. & Simon, M. I. (1994) TIBS 19 485–491). These conserved sequences are made up of the histidine residue that is phosphorylated, followed after approximately 100 residues by a conserved asparagine residue. After another 15 to 45 residues following the asparagine residue, a DXGXG motif is found, followed by a FXXF motif after another 10–20 residues. 10–20 residues further on another glycine motif, GXG is found. The two glycine motifs are thought to be involved in nucleotide binding. This family of histidine kinases includes YEHU protein from _Escherichia coli_.

Response regulators are components of the TCSTS. These proteins are phosphorylated by histidine kinases and in tun, once phosphorylated, effect the response, often through a DNA binding domain that becomes activated. The response regulators are characterized by a conserved N-terminal domain of approximately 100 amino acids. The N-terminal domains of response regulators retain five functionally important residues, corresponding to the residues D12, D13, D57, T87, K109 in CheY (Matsumura, P., Rydel, J. J., Linzmeier, R. & Vacante, D. (1984) J. Bacteriol. 160, 36–41), and have conserved strucal features (Volz, K. (1993) Biochemistry 32, 11741–11753). The 3-dimensional structures of CheY from Salmonella typhimurium (Stock, A. M., Mottonen, J. M., Stock J. B. & Schutt, ,C. E. (1989) Nature, 337, 745–749) and _Escherichia coli_ (Volz, K. & Matsumura, P. (1991) J. Biol. Chem. 266, 15511–15519) and the N-teimnal domain of nitrogen regulatory protein C from _S. typhimurium_ (Volkman, B. F., Nohaile, M. J., Amy, N. K., Kustu, S. & Wemmer, D. E. (1995) Biochemistry, 34 1413–1424), are available, as well as the secondary structure of SpoOF from _Bacillus subtilis_ (Feher, V. A., Zapf, J. W., Hoch, J. A., Dahlquist, F. W., Whiteley, J. M. & Cavanagh, J. (1995) Protein Science, 4, 1801–1814). These structures have an (a/b)5 fold. Several structural residues are conserved between different response regulator sequences, specifically hydrophobic residues within the β-sheet hydrophobic core and sites from α-helical segments.

Among the processes regulated by TCSTS are production of virulence factors, motility, antibiotic resistance and cell replication. bihibitors of TCSTS proteins can prevent the bacterium from establishing and maintaining infection of the host by preventing it from producing the necessary factors for pathogenesis and thereby have utility in anti-bacterial therapy.

Clearly, there is a need for actors, such as the novel compounds of the invention, that have a present benefit of being useful to screen compounds for antibiotic activity. Such factors are also useful to determine their role in pathogenesis of infection, dysfunction and disease. There is also a need for identification and characterization of such factors and their antagonists and agonists which can play a role in preventing, ameliorating or correcting infections, dysfunctions or diseases.

The polypeptides of the invention have amino acid sequence homology to a known YEHU from _Escherichia coli_ protein (see, P33357 from Swissprot database).

SUMMARY OF THE INVENTION

It is an object of the invention to provide polypeptides that have been identified as novel histidine kinase polypeptides by homology between the amino acid sequence set out in Table 1 [SEQ ID NO:2 or SEQ ID NO:3] and a known amino acid sequence or sequences of other proteins such as YEHU from *Escherichia coli* protein.

It is a further object of the invention to provide polynucleotides that encode histidine kinase polypeptides, particularly polynucleotides that encode the polypeptide herein designated histidine kinase.

In a particularly preferred embodiment of the invention the polynucleotide comprises a region encoding histidine kinase polypeptides comprising the sequence set out in Table 1 [SEQ ID NO:1] which includes a full length gene, or a variant thereof.

In another particularly preferred embodiment of the invention there is a novel histidine kinase protein from *Streptococcus pneumoniae* comprising the amino acid sequence of Table 1 [SEQ ID NO:2 or SEQ ID NO:3], or a variant thereof In accordance with another aspect of the invention there is provided an isolated nucleic acid molecule encoding a mature polypeptide expressible by the *Streptococcus pneumoniae* 0100993 strain contained in the deposited strain.

A further aspect of the invention there are provided isolated nucleic acid molecules encoding histidine kinase, particularly *Streptococcus pneumoniae* histidine kinase, including mRNAs, cDNAs, genomic DNAs. Further embodiments of the invention include biologically, diagnostically, prophylactically, clinically or therapeutically useful variants thereof, and compositions comprising the same.

In accordance with another aspect of the invention, there is provided the use of a polynucleotide of the invention for therapeutic or prophylactic purposes, in particular genetic immunization. Among the particularly preferred embodiments of the invention are naturally occurring allelic variants of histidine kinase and polypeptides encoded thereby.

Another aspect of the invention there are provided novel polypeptides of *Streptococcus pneumoniae* referred to herein as histidine kinase as well as biologically, diagnostically, prophylactically, clinically or therapeutically useful variants thereof, and compositions comprising the same.

Among the particularly preferred embodiments of the invention are variants of histidine kinase polypeptide encoded by naturally occurring alleles of the histidine kinase gene.

In a preferred embodiment of the invention there are provided methods for producing the aforementioned histidine kinase polypeptides.

In accordance with yet another aspect of the invention, there are provided inhibitors to such polypeptides, useful as antibacterial agents, including, for example, antibodies.

In accordance with certain preferred embodiments of the invention, there are provided products, compositions and methods for assessing histidine kinase expression, treating disease, for example, otitis media, conjunctivitis, pneumonia, bacteremia, meningitis, sinusitis, pleural empyema and endocarditis, and most particularly meningitis, such as for example infection of cerebrospinal fluid, assaying genetic variation, and administering a histidine kinase polypeptide or polynucleotide to an organism to raise an immunological response against a bacteria, especially a *Streptococcus pneumoniae* bacteria.

In accordance with certain preferred embodiments of this and other aspects of the invention there are provided polynucleotides that hybridize to histidine inase polynucleotide sequences, particularly under stringent conditions.

In certain preferred embodiments of the invention there are provided antibodies against histidine kinase polypeptides.

In other embodiments of the invention there are provided methods for identifying compounds which bind to or otherwise interact with and inhibit or activate an activity of a polypeptide or polynucleotide of the invention comprising: contacting a polypeptide or polynucleotide of the invention with a compound to be screened under conditions to permit binding to or other interaction between the compound and the polypeptide or polynucleotide to assess the binding to or other interaction with the compound, such binding or interaction being associated with a second component capable of providing a detectable signal in response to the binding or interaction of the polypeptide or polynucleotide with the compound; and determining whether the compound binds to or otherwise interacts with and activates or inhibits an activity of the polypeptide or polynucleotide by detecting the presence or absence of a signal generated from the binding or interaction of the compound with the polypeptide or polynucleotide.

In accordance with yet another aspect of the invention, there are provided histidine kinase agonists and antagonists, preferably bacteriostatic or bacteriocidal agonists and antagonists.

In a further aspect of the invention there are provided compositions comprising a histidine kinase polynucleotide or a histidine kinase polypeptide for administration to a cell or to a multicellular organism.

Various changes and modifications within the spit and scope of the disclosed invention will become readily apparent to those skilled in the art from reading the following descriptions and from reading the other parts of the present disclosure.

GLOSSARY

The following definitions are provided to facilitate understanding of certain terms used frequently herein.

"Host cell" is a cell which has been transformed or transfected, or is capable of transformation or transfection by an exogenous polynucleotide sequence.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Gnrffin, A. M., and Griffin, H. G., eds., Humana Press, New Jersey , 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM *J Applied Math*., 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., *Nucleic Acids Research* 12(1): 387 (1984)), BLASTP, BLASTN, and FASTA (Atschul, S. F. et al., *J Molec. Biol.* 215: 403–410 (1990). The BLAST X program is publicly available from NCBI and other sources (BLAST Manual, Altschul, S., et al., NCBI NLM NIH Bethesda, Md. 20894; Altschul, S., et al., *J Mol. Biol.* 215: 403–410 (1990). As an illustration, by a polynucleotide having a nucleotide sequence having at least, for example, 95% "identity" to a reference nucleotide sequence of SEQ ID NO:1 it is intended that the nucleotide sequence of the polynucleotide is identical to the reference sequence except that the polynucleotide sequence may include up to five point mutations per each 100 nucleotides of the reference nucleotide sequence of SEQ ID NO:1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence. Analogously, by a polypeptide having an amino acid sequence having at least, for example, 95% identity to a reference amino acid sequence of SEQ ID NO:2 or SEQ ID NO:3 is intended that the amino acid sequence of the polypeptide is identical to the reference sequence except that the polypeptide sequence may include up to five amino acid alterations per each 100 amino acids of the reference amino acid of SEQ ID NO:2 or SEQ ID NO:3. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. "Polynucleotide(s)" generally refers to any polyribonucleotide or polydeoxribonucleotide, which may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, emymatically or metabolically modified forms of polynucleotides, as well as the chemical forms of DNA and RNA chacteristic of viruses and cells, including, for example, simple and complex cells. "Polynucleotide(s)" also embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma carboxylation of glutamic acid residues, hydroxylation and ADP-ribosylation, selenoylation, sulfation, transfer-RNA mediated addition of amino acids to proteins, such as arginylation, and ubiquitination. See, for instance, *PROTEINS—STRUCTURE AND MOLECULAR PROPERTIES*, 2nd Ed., T. E. Creighton, W. H. Freeman and Company, New York (1993) and Wold, F., Posttranslational Protein Modifications: Perspectives and Prospects, pgs. 1–12 in *POSTTRANSLATIONAL COVALENT MODIPYCATION OF PROTEINS*, B. C. Johnson, Ed., Academic Press, New York (1983); Seifter et al., *Meth. Enzymol.* 182:626–646 (1990) and Rattan et al., *Protein Synthesis:*

*Posttranslational Modifications and Aging*, Ann. N.Y. Acad. Sci. 663: 48–62 (1992). Polypeptides may be branched or cyclic, with or without branching. Cyclic, branched and branched circular polypeptides may result from post-translational natural processes and may be made by entirely synthetic methods, as well.

"Variant(s)" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

DESCRIPTION OF THE INVENTION

The invention relates to novel histidine kinase polypeptides and polynucleotides as described in greater detail below. In particular, the invention relates to polypeptides and polynucleotides of a novel histidine kinase of *Streptococcus pneumoniae*, which is related by amino acid sequence homology to YEHU from *Escherichia coli* polypeptide. The invention relates especially to histidine kinase having the nucleotide and amino acid sequences set out in Table 1 [SEQ ID NO:1] and Table 1 [SEQ ID NO:2 or SEQ ID NO:3] respectively, and to the histidine kinase nucleotide sequences of the DNA in the deposited strain and amino acid sequences encoded thereby.

TABLE 1

Histidine kinase Polynucleotide and Polypeptide Sequences (A) Sequences from *Streptococcus pneumoniae* histidine kinase polynucleotide sequence [SEQ ID NO: 1]

```
   5'-1 GAAAAGACC CTGTCACCTG AGGAGTATGC AGTTACCCAG GAAAATCAAA
     51 CAGAACGAGC TTTCTCAAAC CGTTACTGGG ATAAATTTGA ATCCGGTATC
    101 TATGTGGATA TAGCAACTGG GGAACCTCTC TTTTCATCAA AAGACAAATT
    151 TGAGTCTGGT TGTGGCTGGC CTAGTTTTAC CCAACCCATC AGTCCAGATG
    201 TTGTCACCTA CAAGGAAGAT AAGTCCTACA ATATGACGCG TATGGAAGTG
    251 CGGAGCCGAG TAGGAGATTC TCACCTTGGG CATGTCTTTA CGGATGGTCC
    301 ACAGGACAAG GGCGGCTTAC GTTACTGTAT CAATAGCCTC TCTATCCGCT
    351 TTATTCCCAA AGACCAAATG GAAGAAAAAG GCTACGCTTA TTTACTAGAT
    401 TATGTTGATT AATACTCTTC GAAAATCTCT TCAAACCACG TCAGCGTCGC
    451 CTTACCGTAT GTAGGGTTAC TGACTCCGTC AGTTTTATCT ACAACCTCAA
    501 AGCTATACTT TGAGCTGACT TCGTCAGTTT TATCTACAAC CTCAAAGCGG
    551 TACTTTGAGA AACCTGTGGC TATCTTCCTA GTTTACTTTT TGATTTTTAT
    601 TGAGTATAAG AGGTCTTTCC TAAGCAGTTA GAGGAGAATT TTGCTATACT
    651 GATACTAGTA AGTGGTAAAG GAGCAGAGCA TGACCTACAC AATCTTAATC
    701 GTAGAAGATG AATATCTGGT AAGACAAGGT TTGACTAAAC TGGTCAATGT
    751 AGCAGCCTAC GATATGGAAA TCATCGGTCA GGCTGAAAAT GGAAGGCAGG
    801 CTTGGGAATT GATCCAAAAG CAGGTTCCAG ATATCATTTT AACCGATATC
    851 AACATGCCTC ATCTAAATGG CATCCAGTTG GCCAGTCTGG TACGAGAAAC
    901 CTATCCTCAG GTTCATTTGG TCTTTTTAAC AGGTTACGAT GATTTTGATT
    951 ATGCCTTGTC TGCTGTCAAA CTAGGTGTGG ACGACTACCT GCTCAAACCC
   1001 TTTTCTCGTC AGGATATTGA GGAAATGTTG GGGAAAATCA AACAAAAACT
   1051 AGACAAGGAA GAGAAAGAAG AGCAGTTACA AGATTTATTG ACTAATAGGT
   1101 TTGAAGGAAA CATGGCCCAG AAAATCCAGT CTCATCTGGC TGATAGCCAA
```

TABLE 1-continued

Histidine kinase Polynucleotide and Polypeptide Sequences

```
1151 TTTAGTTTAA AGTCTTTAGC CAGTGACTTA GGTTTTAGTC CGACCTATCT
1201 GAGTTCCTTG ATTAAGAAAG AGTTGGGCTT GCCTTTTCAG GATTATCTAG
1251 TGAGAGAACG TGTTAAACAA GCCAAGCTCT TGCTTTTAAC TACAGATCTG
1301 AAGATTTATG AGATCGCAGA GAAGGTTGGT TTTGAAGATA TGAACTATTT
1351 TACCCAACGT TTTAAGCAGA TTGCAGGTGT GACACCTCGT CAGTTTAAGA
1401 AGGGAGAAGA CCGATGAAGC GTTCTTCTCT TTTAGTTAGA ATGGTTATTT
1451 CCATCTTTCT GGTCTTTCTC ATTCTCCTAG CTCTGGTTGG AACTTTCTAC
1501 TATCAATCAA GTTCTTCAGC CATTGAGGCC ACCATTGAGG GCAACAGCCA
1551 AACGACCATC AGCCAGACTA GCCACTTTAT TCAGTCTTAT ATCAAAAAAC
1601 TAGAAACCAC TTCGACCGGT TGACCCAGC AGACGGATGT TCTGGCCTAT
1651 GCTGAGAATC CCAGTCAAGA CAAGGTCGAG GGAATCCGAG ATTTGTTTTT
1701 GACCATCTTG AAGTCAGATA AGGACTTGAA AACTGTTGTG CTGGTGACCA
1751 AATCTGGTCA GGTCATTTCT ACAGATGACA GTGTGCAGAT GAAAACTTCC
1801 TCTGATATGA TGGCTGAGGA TTGGTACCAA AAGGCCATTC ATCAGGGAGT
1851 GATGCCTGTT TTGACTCCAG CTCGTAAATC AGATAGTCAG TGGGTCATTT
1901 CTGTCACTCA AGAACTTGTT GATGCAAAGG GAGCCAATCT TGGTGTGCTT
1951 CGTTTGGATA TTTCTTATGA AACTCTGGAA GCCTATCTCA ATCAACTCCA
2001 GTTGGGGCAG CAGGGCTTTG CCTTCATTAT CAATGAAAAC CATGAATTTG
2051 TCTACCATCC TCAACACACA GTTTATAGTT CGTCTAGCAA AATGGAGGCT
2101 ATGAAACCCT ACATCGAGAC AGGTCAGGGT TATACTCCTG GTCACAAATC
2151 CTACGTCAGT CAAGAGAAGA TTGCAGGAAC TGATTGGACG GTACTTGGCG
2201 TGTCATCATT GGAAAAGTTA GACCAGGTTC GGAGTCAGCT CTTGTGGACC
2251 TTGCTTGGGG CCAGTGTCAC ATCTCTTCTT GTCTGTCTCT GCTTAGTGTG
2301 GTTCAGTCTT AAACGCTGGA TTGCTCCTTT GAAGGATTTG AGAGAAACCA
2351 TGTTGGAAAT TGCTTCTGGT GCTCAAAATC TTCGTGCCAA GGAAGTTGGT
2401 GCCTATGAAC TGAGAGAAGT AACTCGCCAA TTTAATGCCA TGTTGGATCA
2451 GATTGATCAG TTGATGGTAG CTATTCGTAG CCAGGGAGAA ACGACCCGTC
2501 AGTACCAACT TCAAGCCCTT TCGAGCCAGA TTAATCCACA TTTCCTCTAT
2551 AACACTTTGG ACACCATCAT CTGGATGGCT GAATTTCATG ATAGTCAGCG
2601 AGTGGTGCAG GTGACCAAGT CCTTGGCAAC CTATTTCCGC TTGGCACTCA
2651 ATCAAGGCAA AGACTTGATT TGTCTCTCTG ACGAAATCAA TCATGTCCGC
2701 CAGTATCTCT TTATCCAGAA ACAACGCTAT GGAGATAAGC TGGAATACGA
2751 AATTAATGAA AATGTTGCCT TTGATAATTT AGTCTTACCC AAGCTGGTCC
2801 TACAACCCCT TGTAGAAAAT GCTCTTTACC ATGGCATTAA GGAAAAGGAA
2851 GGTCAGGGCC ATATTAAACT TTCTGTCCAG AAACAGGATT CGGGATTGGT
2901 CATCCGTATT GAGGATGATG GCGTTGGCTT CCAAAATGCT GGTGATAGTA
2951 GTCAAAGTCA ACTCAAACGT GGGGGAGTTG GTCTTCAAAA TGTCGATCAA
3001 CGGCTCAAAC TTCATTTTGG AGCCAATTAC CAGATGAAGA TTGATTCTAC
```

TABLE 1-continued

Histidine kinase Polynucleotide and Polypeptide Sequences

```
     3051 ACCCCAAAAA GGGACGAAAG TTGAAATATA TATAAATACA GTAGAAACTA

3101 GATAACTCCC AGTCAATTCT GGGAGTCTTA TGCGT

-3'
```

(B) Histidine kinase polypeptide sequence deduced from the polynucleotide sequence in this table, first reading frame
[SEQ ID NO: 2]

```
          NH2

1 MVISIFLVFL ILLALVGTFY YQSSSSAIEA TIEGNSQTTI SQTSHFIQSY

51 IKKLETTSTG LTQQTDVLAY AENPSQDKVE GIRDLFLTIL KSDKDLKTVV

101 LVTKSGQVIS TDDSVQMKTS SDMMAEDWYQ KAIHQGVMPV LTPARKSDSQ

151 WVISVTQELV DAKGANLGVL RLDISYETLE AYLNQLQLGQ QGFAFIINEN

201 HEFVYHPQHT VYSSSSKMEA MKPYIETGQG YTPGHKSYVS QEKIAGTDWT

251 VLGVSSLEKL DQVRSQLLWT LLGASVTSLL VCLCLVWFSL KRWIAPLKDL

301 RETMLEIASG AQNLRAKEVG AYELREVTRQ FNAMLDQIDQ LMVAIRSQGE

351 TTRQYQLQAL SSQINPHFLY NTLDTIIWMA EFHDSQRVVQ VTKSLATYFR

401 LALNQGKDLI CLSDEINHVR QYLFIQKQRY GDKLEYEINE NVAFDNLVLP

451 KLVLQPLVEN ALYHGIKEKE GQGHIKLSVQ KQDSGLVIRI EDDGVGFQNA

501 GDSSQSQLKR GGVGLQNVDQ RLKLHFGANY QMKIDSTPQK GTKVEIYINT

551 VETR-COOH
```

(C) Histidine kinase polypeptide sequence deduced from the polynucleotide sequence in this table, second reading frame
[SEQ ID NO: 3]

```
        1 MKRSSLLVRM VISIFLVFLI LLALVGTFYY QSSSSAIEAT IEGNSQTTIS

51 QTSHFIQSYI KKLETTSTGL TQQTDVLAYA ENPSQDKVEG IRDLFLTILK

101 SDKDLKTVVL VTKSGQVIST DDSVQMKTSS DMMAEDWYQK AIHQGVMPVL

151 TPARKSDSQW VISVTQELVD AKGANLGVLR LDISYETLEA YLNQLQLGQQ

201 GFAFIINENH EFVYHPQHTV YSSSSKMEAM KPYIETGQGY TPGHKSYVSQ

251 EKIAGTDWTV LGVSSLEKLD QVRSQLLWTL LGASVTSLLV CLCLVWFSLK

301 RWIAPLKDLR ETMLEIASGA QNLRAKEVGA YELREVTRQF NAMLDQIDQL

351 MVAIRSQGET TRQYQLQALS SQINPHFLYN TLDTIIWMAE FHDSQRVVQV

401 TKSLATYFRL ALNQGKDLIC LSDEINHVRQ YLFIQKQRYG DKLEYEINEN

451 VAFDNLVLPK LVLQPLVENA LYHGIKEKEG QGHIKLSVQK QDSGLVIRIE

501 DDGVGFQNAG DSSQSQLKRG GVGLQNVDQR LKLHFGANYQ MKIDSTPQKG

551 TKVEIYINTB ETR
```

(D) Polynucleotide sequence embodiments [SEQ ID NO: 1]

```
  X-(R1)n-1 GAAAAGACC CTGTCACCTG AGGAGTATGC AGTTACCCAG GAAAATCAAA

51 CAGAACGAGC TTTCTCAAAC CGTTACTGGG ATAAATTTGA ATCCGGTATC

101 TATGTGGATA TAGCAACTGG GGAACCTCTC TTTTCATCAA AAGACAAATT

151 TGAGTCTGGT TGTGGCTGGC CTAGTTTTAC CCAACCCATC AGTCCAGATG

201 TTGTCACCTA CAAGGAAGAT AAGTCCTACA ATATGACGCG TATGGAAGTG

251 CGGAGCCGAG TAGGAGATTC TCACCTTGGG CATGTCTTTA CGGATGGTCC

301 ACAGGACAAG GGCGGCTTAC GTTACTGTAT CAATAGCCTC TCTATCCGCT
```

TABLE 1-continued

Histidine kinase Polynucleotide and Polypeptide Sequences

```
 351 TTATTCCCAA AGACCAAATG GAAGAAAAAG GCTACGCTTA TTTACTAGAT
 401 TATGTTGATT AATACTCTTC GAAAATCTCT TCAAACCACG TCAGCGTCGC
 451 CTTACCGTAT GTAGGGTTAC TGACTCCGTC AGTTTTATCT ACAACCTCAA
 501 AGCTATACTT TGAGCTGACT TCGTCAGTTT TATCTACAAC CTCAAAGCGG
 551 TACTTTGAGA AACCTGTGGC TATCTTCCTA GTTTACTTTT TGATTTTTAT
 601 TGAGTATAAG AGGTCTTTCC TAAGCAGTTA GAGGAGAATT TGCTATACT
 651 GATACTAGTA AGTGGTAAAG GAGCAGAGCA TGACCTACAC AATCTTAATC
 701 GTAGAAGATG AATATCTGGT AAGAGAAGGT TTGACTAAAC TGGTCAATGT
 751 AGCAGCCTAC GATATGGAAA TCATCGGTCA GGCTGAAAAT GGAAGGCAGG
 801 CTTGGGAATT GATCCAAAAG CAGGTTCCAG ATATCATTTT AACCGATATC
 851 AACATGCCTC ATCTAAATGG CATCCAGTTG GCCAGTCTGG TACGAGAAAC
 901 CTATCCTCAG GTTCATTTGG TCTTTTTAAC AGGTTACGAT GATTTTGATT
 951 ATGCCTTGTC TGCTGTCAAA CTAGGTGTGG ACGACTACCT GCTCAAACCC
1001 TTTTCTCGTC AGGATATTGA GGAAATGTTG GGGAAAATCA AACAAAAACT
1051 AGACAAGGAA GAGAAAGAAG AGCAGTTACA AGATTTATTG ACTAATAGGT
1101 TTGAAGGAAA CATGGCCCAG AAAATCCAGT CTCATCTGGC TGATAGCCAA
1151 TTTAGTTTAA AGTCTTTAGC CAGTGACTTA GGTTTTAGTC CGACCTATCT
1201 GAGTTCCTTG ATTAAGAAAG AGTTGGGCTT GCCTTTTCAG GATTATCTAG
1251 TGAGAGAACG TGTTAAACAA GCCAAGCTCT TGCTTTTAAC TACAGATCTG
1301 AAGATTTATG AGATCGCAGA GAAGGTTGGT TTTGAAGATA TGAACTATTT
1351 TACCCAACGT TTTAAGCAGA TTGCAGGTGT GACACCTCGT CAGTTTAAGA
1401 AGGGAGAAGA CCGATGAAGC GTTCTTCTCT TTTAGTTAGA ATGGTTATTT
1451 CCATCTTTCT GGTCTTTCTC ATTCTCCTAG CTCTGGTTGG AACTTTCTAC
1501 TATCAATCAA GTTCTTCAGC CATTGAGGCC ACCATTGAGG GCAACAGCCA
1551 AACGACCATC AGCCAGACTA GCCACTTTAT TCAGTCTTAT ATCAAAAAAC
1601 TAGAAACCAC TTCGACCGGT TTGACCCAGC AGACGGATGT TCTGGCCTAT
1651 GCTGAGAATC CCAGTCAAGA CAAGGTCGAG GGAATCCGAG ATTTGTTTTT
1701 GACCATCTTG AAGTCAGATA AGGACTTGAA AACTGTTGTG CTGGTGACCA
1751 AATCTGGTCA GGTCATTTCT ACAGATGACA GTGTGCAGAT GAAAACTTCC
1801 TCTGATATGA TGGCTGAGGA TTGGTACCAA AAGGCCATTC ATCAGGGAGT
1851 GATGCCTGTT TTGACTCCAG CTCGTAAATC AGATAGTCAG TGGGTCATTT
1901 CTGTCACTCA AGAACTTGTT GATGCAAAGG GAGCCAATCT TGGTGTGCTT
1951 CGTTTGGATA TTTCTTATGA AACTCTGGAA GCCTATCTCA ATCAACTCCA
2001 GTTGGGGCAG CAGGGCTTTG CCTTCATTAT CAATGAAAAC CATGAATTTG
2051 TCTACCATCC TCAACACACA GTTTATAGTT CGTCTAGCAA AATGGAGGCT
2101 ATGAAACCCT ACATCGAGAC AGGTCAGGGT TATACTCCTG GTCACAAATC
2151 CTACGTCAGT CAAGAGAAGA TTGCAGGAAC TGATTGGACG GTACTTGGCG
2201 TGTCATCATT GGAAAAGTTA GACCAGGTTC GGAGTCAGCT CTTGTGGACC
2251 TTGCTTGGGG CCAGTGTCAC ATCTCTTCTT GTCTGTCTCT GCTTAGTGTG
```

TABLE 1-continued

Histidine kinase Polynucleotide and Polypeptide Sequences

```
2301 GTTCAGTCTT AAACGCTGGA TTGCTCCTTT GAAGGATTTG AGAGAAACCA

2351 TGTTGGAAAT TGCTTCTGGT GCTCAAAATC TTCGTGCCAA GGAAGTTGGT

2401 GCCTATGAAC TGAGAGAAGT AACTCGCCAA TTTAATGCCA TGTTGGATCA

2451 GATTGATCAG TTGATGGTAG CTATTCGTAG CCAGGGAGAA ACGACCCGTC

2501 AGTACCAACT TCAAGCCCTT TCGAGCCAGA TTAATCCACA TTTCCTCTAT

2551 AACACTTTGG ACACCATCAT CTGGATGGCT GAATTTCATG ATAGTCAGCG

2601 AGTGGTGCAG GTGACCAAGT CCTTGGGAAC CTATTTCCGC TTGGCACTCA

2651 ATCAAGGCAA AGACTTGATT TGTCTCTCTG ACGAAATCAA TCATGTCCGC

2701 CAGTATCTCT TTATCCAGAA ACAACGCTAT GGAGATAAGC TGGAATACGA

2751 AATTAATGAA AATGTTGCCT TTGATAATTT AGTCTTACCC AAGCTGGTCC

2801 TACAACCCCT TGTAGAAAAT GCTCTTTACC ATGGCATTAA GGAAAAGGAA

2851 GGTCAGGGCC ATATTAAACT TTCTGTCCAG AAACAGGATT CGGGATTGGT

2901 CATCCGTATT GAGGATGATG GCGTTGGCTT CCAAAATGCT GGTGATAGTA

2951 GTCAAAGTCA ACTCAAACGT GGGGGAGTTG GTCTTCAAAA TGTCGATCAA

3001 CGGCTCAAAC TTCATTTTGG AGCCAATTAC CAGATGAAGA TTGATTCTAC

3051 ACCCCAAAAA GGGACGAAAG TTGAAATATA TAAATACA GTAGAAACTA

3101 GATAACTCCC AGTCAATTCT GGGAGTCTTA TGCGT
```

-(R₂)ₙ-Y (E) Polypeptide sequence embodiments [SEQ ID NO: 2]
X-(R₁)₁-

```
  1 MVISIFLVFL ILLALVGTFY YQSSSSAIEA TIEGNSQTTI SQTSHFIQSY

51 IKKLETTSTG LTQQTDVLAY AENPSQDKVE GIRDLFLTIL KSDKDLKTVV

101 LVTKSGQVIS TDDSVQMKTS SDMMAEDWYQ KAIHQGVMPV LTPARKSDSQ

151 WVISVTQELV DAKGANLGVL RLDISYETLE AYLNQLQLGQ QGFAFIINEN

201 HEFVYHPQHT VYSSSSKMEA MKPYIETGQG YTPGHKSYVS QEKIAGTDWT

251 VLGVSSLEKL DQVRSQLLWT LLGASVTSLL VCLCLVWFSL KRWIAPLKDL

301 RETMLEIASG AQNLRAKEVG AYELREVTRQ FNAMLDQIDQ LMVAIRSQGE

351 TTRQYQLQAL SSQINPHFLY NTLDTIIWMA EFHDSQRVVQ VTKSLATYFR

401 LALNQGKDLI CLSDEINHVR QYLFIQKQRY GDKLEYEINE NVAFDNLVLP

451 KLVLQPLVEN ALYHGIKEKE GQGHIKLSVQ KQDSGLVIRI EDDGVGFQNA

501 GDSSQSQLKR GGVGLQNVDQ RLKLHFGANY QMKIDSTPQK GTKVEIYINT

551 VETR-(R₂)ₙ-Y
```

(F) Polypeptide sequence embodiments [SEQ ID NO: 3]
X-(R₁)₁-

```
  1 MKRSSLLVRM VISIFLVFLI LLALVGTFYY QSSSSAIEAT IEGNSQTTIS

51 QTSHFIQSYI KKLETTSTGL TQQTDVLAYA ENPSQDKVEG IRDLFLTILK

101 SDKDLKTVVL VTKSGQVIST DDSVQMKTSS DMMAEDWYQK AIHQGVMPVL

151 TPARKSDSQW VISVTQELVD AKGANLGVLR LDISYETLEA YLNQLQLGQQ

201 GFAFIINENH EFVYHPQHTV YSSSSKMEAM KPYIETGQGY TPGHKSYVSQ
```

TABLE 1-continued

Histidine kinase Polynucleotide and Polypeptide Sequences

```
    251 EKIAGTDWTV LGVSSLEKLD QVRSQLLWTL LGASVTSLLV CLCLVWFSLK

301 RWIAPLKDLR ETMLEIASGA QNLRAKEVGA YELREVTRQF NAMLDQIDQL

351 MVAIRSQGET TRQYQLQALS SQINPHFLYN TLDTIIWMAE FHDSQRVVQV

401 TKSLATYFRL ALNQGKDLIC LSDEINHVRQ YLFIQKQRYG DKLEYEINEN

451 VAFDNLVLPK LVLQPLVENA LYHGIKEKEG QGHIKLSVQK QDSGLVIRIE

501 DDGVGFQNAG DSSQSQLKRG GVGLQNVDQR LKLHFGANYQ MKIDSTPQKG

551 TKVEIYINTV ETR-(R2)n-Y
```

(G) Polynucleotide sequence from *Streptococcus pneumoniae* Response regulator [SEQ ID NO: 4], cognate of the Histidine kinase of the invention

```
 5'-1 GAAAAAGACC CTGTCACCTG AGGAGTATGC AGTTACCCAG GAAAATCAAA

51 CAGAACGAGC TTTCTCAAAC CGTTACTGGG ATAAATTTGA ATCCGGTATC

101 TATGTGGATA TAGCAACTGG GGAACCTCTC TTTTCATCAA AAGACAAATT

151 TGAGTCTGGT TGTGGCTGGC CTAGTTTTAC CCAACCCATC AGTCCAGATG

201 TTGTCACCTA CAAGGAAGAT AAGTCCTACA ATATGACGCG TATGGAAGTG

251 CGGAGCCGAG TAGGAGATTC TCACCTTGGG CATGTCTTTA CGGATGGTCC

301 ACAGGACAAG GGCGGCTTAC GTTACTGTAT CAATAGCCTC TCTATCCGCT

351 TTATTCCCAA AGACCAAATG GAAGAAAAAG GCTACGCTTA TTTACTAGAT

401 TATGTTGATT AATACTCTTC GAAAATCTCT TCAAACCACG TCAGCGTCGC

451 CTTACCGTAT GTAGGGTTAC TGACTCCGTC AGTTTTATCT ACAACCTCAA

501 AGCTATACTT TGAGCTGACT TCGTCAGTTT TATCTACAAC CTCAAAGCGG

551 TACTTTGAGA AACCTGTGGC TATCTTCCTA GTTTACTTTT TGATTTTTAT

601 TGAGTATAAG AGGTCTTTCC TAAGCAGTTA GAGGAGAATT TTGCTATACT

651 GATACTAGTA AGTGGTAAAG GAGCAGAGCA TGACCTACAC AATCTTAATC

701 GTAGAAGATG AATATCTGGT AAGACAAGGT TTGACTAAAC TGGTCAATGT

751 AGCAGCCTAC GATATGGAAA TCATCGGTCA GGCTGAAAAT GGAAGGCAGG

801 CTTGGGAATT GATCCAAAAG CAGGTTCCAG ATATCATTTT AACCGATATC

851 AACATGCCTC ATCTAAATGG CATCCAGTTG GCCAGTCTGG TACGAGAAAC

901 CTATCCTCAG GTTCATTTGG TCTTTTTAAC AGGTTACGAT GATTTTGATT

951 ATGCCTTGTC TGCTGTCAAA CTAGGTGTGG ACGACTACCT GCTCAAACCC

1001 TTTTCTCGTC AGGATATTGA GGAAATGTTG GGGAAAATCA AACAAAAACT

1051 AGACAAGGAA GAGAAAGAAG AGCAGTTACA AGATTTATTG ACTAATAGGT

1101 TTGAAGGAAA CATGGCCCAG AAAATCCAGT CTCATCTGGC TGATAGCCAA

1151 TTTAGTTTAA AGTCTTTAGC CAGTGACTTA GGTTTTAGTC CGACCTATCT

1201 GAGTTCCTTG ATTAAGAAAG AGTTGGGCTT GCCTTTTCAG GATTATCTAG

1251 TGAGAGAACG TGTTAAACAA GCCAAGCTCT TGCTTTTAAC TACAGATCTG

1301 AAGATTTATG AGATCGCAGA GAAGGTTGGT TTTGAAGATA TGAACTATTT

1351 TACCCAACGT TTTAAGCAGA TTGCAGGTGT GACACCTCGT CAGTTTAAGA

1401 AGGGAGAAGA CCGATGAAGC GTTCTTCTCT TTTAGTTAGA ATGGTTATTT

1451 CCATCTTTCT GGTCTTTCTC ATTCTCCTAG CTCTGGTTGG AACTTTCTAC
```

TABLE 1-continued

Histidine kinase Polynucleotide and Polypeptide Sequences

```
1501 TATCAATCAA GTTCTTCAGC CATTGAGGCC ACCATTGAGG GCAACAGCCA

1551 AACGACCATC AGCCAGACTA GCCACTTTAT TCAGTCTTAT ATCAAAAAC

1601 TAGAAACCAC TTCGACCGGT TTGACCCAGC AGACGGATGT TCTGGCCTAT

1651 GCTGAGAATC CCAGTCAAGA CAAGGTCGAG GGAATCCGAG ATTTGTTTTT

1701 GACCATCTTG AAGTCAGATA AGGACTTGAA AACTGTTGTG CTGGTGACCA

1751 AATCTGGTCA GGTCATTTCT ACAGATGACA GTGTGCAGAT GAAAACTTCC

1801 TCTGATATGA TGGCTGAGGA TTGGTACCAA AAGGCCATTC ATCAGGGAGT

1851 GATGCCTGTT TTGACTCCAG CTCGTAAATC AGATAGTCAG TGGGTCATTT

1901 CTGTCACTCA AGAACTTGTT GATGCAAAGG GAGCCAATCT TGGTGTGCTT

1951 CGTTTGGATA TTTCTTATGA AACTCTGGAA GCCTATCTCA ATCAACTCCA

2001 GTTGGGGCAG CAGGGCTTTG CCTTCATTAT CAATGAAAAC CATGAATTTG

2051 TCTACCATCC TCAACACACA GTTTATAGTT CGTCTAGCAA AATGGAGGCT

2101 ATGAAACCCT ACATCGAGAC AGGTCAGGGT TATACTCCTG GTCACAAATC

2151 CTACGTCAGT CAAGAGAAGA TTGCAGGAAC TGATTGGACG GTACTTGGCG

2201 TGTCATCATT GGAAAAGTTA GACCAGGTTC GGAGTCAGCT CTTGTGGACC

2251 TTGCTTGGGG CCAGTGTCAC ATCTCTTCTT GTCTGTCTCT GCTTAGTGTG

2301 GTTCAGTCTT AAACGCTGGA TTGCTCCTTT GAAGGATTTG AGAGAAACCA

2351 TGTTGGAAAT TGCTTCTGGT GCTCAAAATC TTCGTGCCAA GGAAGTTGGT

2401 GCCTATGAAC TGAGAGAAGT AACTCGCCAA TTTAATGCCA TGTTGGATCA

2451 GATTGATCAG TTGATGGTAG CTATTCGTAG CCAGGGAGAA ACGACCCGTC

2501 AGTACCAACT TCAAGCCCTT TCGAGCCAGA TTAATCCACA TTTCCTCTAT

2551 AACACTTTGG ACACCATCAT CTGGATGGCT GAATTTCATG ATAGTCAGCG

2601 AGTGGTGCAG GTGACCAAGT CCTTGGCAAC CTATTTCCGC TTGGCACTCA

2651 ATCAAGGCAA AGACTTGATT TGTCTCTCTG ACGAAATCAA TCATGTCCGC

2701 CAGTATCTCT TTATCCAGAA ACAACGCTAT GGAGATAAGC TGGAATACGA

2751 AATTAATGAA AATGTTGCCT TGATAATTT AGTCTTACCC AAGCTGGTCC

2801 TACAACCCCT TGTAGAAAAT GCTCTTTACC ATGGCATTAA GGAAAAGGAA

2851 GGTCAGGGCC ATATTAAACT TTCTGTCCAG AAACAGGATT CGGGATTGGT

2901 CATCCGTATT GAGGATGATG GCGTTGGCTT CCAAAATGCT GGTGATAGTA

2951 GTCAAAGTCA ACTCAAACGT GGGGGAGTTG GTCTTCAAAA TGTCGATCAA

3001 CGGCTCAAAC TTCATTTTGG AGCCAATTAC CAGATGAAGA TTGATTCTAC

3051 ACCCCAAAAA GGGACGAAAG TTGAAATATA TATAAATACA GTAGAAACTA

3101 GATAACTCCC AGTCAATTCT GGGAGTCTTA TGCGT-3'
```

(H) Polypeptide sequences from *Streptococcus pneumoniae*
Response regulator [SEQ ID NO: 5] deduced from the polynucleotide of SEQ ID NO: 4, cognate of the Histidine kinase of the invention.

```
NH₂-1 MTYTILIVED EYLVRQGLTK LVNVAAYDME IIGQAENGRQ AWELIQKQVP

51 DIILTDINMP HLNGIQLASL VRETYPQVHL VFLTGYDDFD YALSAVKLGV
```

TABLE 1-continued

Histidine kinase Polynucleotide and Polypeptide Sequences

```
101 DDYLLKPFSR QDIEEMLGKI KQKLDKEEKE EQLQDLLTNR FEGNMAQKIQ

151 SHLADSQFSL KSLASDLGFS PTYLSSLIKK ELGLPFQDYL VRERVKQAKL

201 LLLTTDLKIY EIAEKVGFED MNYFTQRFKQ IAGVTPRQFK KGEDR-COOH
```

Deposited Materials

A deposit containing a *Streptococcus pneumoniae* 0100993 strain has been deposited with the National Collections of Industrial and Marine Bacteria Ltd. (herein "NCIMB"), 23 St. Machar Drive, Aberdeen AB2 1RY, Scotland on Apr. 11, 1996 and assigned deposit number 40794. The deposit was described as *Streptococcus peumnoniae* 0100993 on deposit. On Apr. 17, 1996 a *Streptococcus peumnoniae* 0100993 DNA library in *E. coli* was similarly deposited with the NCIMB and assigned deposit number 40800. The *Streptococcus pneumoniae* strain deposit is referred to herein as "the deposited strain" or as "the DNA of the deposited rain."

The deposited strain contains the full length histidine kinase gene. The sequence of the polynucleotides contained in the deposited strain, as well as the amino acid sequence of the polypeptide encoded thereby, are controlling in the event of any conflict with any description of sequences herein.

The deposit of the deposited strain has been made under the terms of the Budapest Treaty on the International Recognition of the Deposit of Micro-organisms for Purposes of Patent Procedure. The strain will be irrevocably and without restriction or condition released to the public upon the issuance of a patent. The deposited strain is provided merely as convenience to those of skill in the art and is not an admission that a deposit is required for enablement, such as that required under 35 U.S.C. §112.

A license may be required to make, use or sell the deposited strain, and compounds derived therefrom, and no such license is hereby granted.

Polypeptides

The polypeptides of the invention include the polypeptide of Table 1 [SEQ ID NO:2 or SEQ ID NO:3] (in particular the mature polypeptide) as well as polypeptides and fragments, particularly those which have the biological activity of histidine kinase, and also those which have at least 70% identity to the polypeptide of Table 1 [SEQ ID NO:2 or SEQ ID NO:3] or the relevant portion, preferably at least 80% identity to the polypeptide of Table 1 [SEQ ID NO:2 or SEQ ID NO:3], and more preferably at least 90% similarity (more preferably at least 90% identity) to the polypeptide of Table 1 [SEQ ID NO:2 or SEQ ID NO:3] and still more preferably at least 95% similarity (still more preferably at least 95% identity) to the polypeptide of Table 1 [SEQ ID NO:2 or SEQ ID NO:3] and also include portions of such polypeptides with such portion of the polypeptide generally containing at least 30 amino acids and more preferably at least 50 amino acids.

The invention also includes polypeptides of the formula set forth in Table 1 (D) wherein, at the amino terminus, X is hydrogen, and at the carboxyl terminus, Y is hydrogen or a metal, $R_1$ and $R_2$ is any amino acid residue, and n is an integer between 1 and 1000. Any stretch of amino acid residues denoted by either R group, where R is greater than 1, may be either a heteropolymer or a homopolymer, preferably a heteropolymer.

A fragment is a variant polypeptide having an amino acid sequence that entirely is the same as part but not all of the amino acid sequence of the aforementioned polypeptides. As with histidine kinase polypeptides fragments may be "freestanding," or comprised within a larger polypeptide of which they form a part or region, most preferably as a single continuous region, a single larger polypeptide.

Preferred fragments include, for example, truncation polypeptides having a portion of the amino acid sequence of Table 1 [SEQ ID NO:2 or SEQ ID NO:3], or of variants thereof, such as a continuous series of residues that includes the amino terminus, or a continuous series of residues that includes the carboxyl terminus. Degradation forms of the polypeptides of the invention in a host cell, particularly a *Streptococcus pneumoniae*, are also preferred. Further preferred are fragments characterized by structural or functional attributes such as fragments that comprise alpha-helix and alpha-helix forming regions, beta-sheet and beta-sheet-forming regions, tum and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Also preferred are biologically active fragments which are those fragments that mediate activities of histidine kinase, including those with a similar activity or an improved activity, or with a decreased undesirable activity. Also included are those fragments that are antigenic or immunogenic in an animal, especially in a human. Particularly preferred are fragments comprising receptors or domains of enzymes that confer a function essential for viability of *Streptococcus pneumoniae* or the ability to initiate, or maintain cause disease in an individual, particularly a human.

Variants that are fragments of the polypeptides of the invention may be employed for producing the corresponding full-length polypeptide by peptide synthesis; therefore, these variants may be employed as intermediates for producing the full-length polypeptides of the invention.

Polynucleotides

Another aspect of the invention relates to isolated polynucleotides, including the full length gene, that encode the histidine kinase polypeptide having the deduced amino acid sequence of Table 1 [SEQ ID NO:2 or SEQ ID NO:3] and polynucleotides closely related thereto and variants thereof Using the information provided herein, such as the polynucleotide sequence set out in Table 1 [SEQ ID NO:1], a polynucleotide of the invention encoding histidine kinase polypeptide may be obtained using standard cloning and screening methods, such as those for cloning and sequencing chromosomal DNA fragments from bacteria using *Streptococcus pneumoniae* 0100993 cells as starting material, followed by obtaining a full length clone. For example, to obtain a polynucleotide sequence of the invention, such as the sequence given in Table 1 [SEQ ID NO:1], typically a library of clones of chromosomal DNA of *Streptococcus pneumoniae* 0100993 in *E. coli* or some other suitable host is probed with a radiolabeled oligonucleotide, preferably a 17-mer or longer, derived from a partial sequence. Clones carrying DNA identical to that of the probe can then be distinguished using stringent conditions. By sequencing the individual clones thus identified with sequencing primers designed from the original sequence it is then possible to extend the sequence in both directions to determine the full gene sequence. Conveniently, such sequencing is performed using denatured double stranded DNA prepared from a plasmid clone. Suitable techniques are described by Maniatis, T., Fritsch, E. F. and Sambrook et al., *MOLECULAR CLONING, A LABORATORY MANUAL*, 2nd Ed.; Cold Spring Harbor Laboratory Press, Cold Spring Harbor, N.Y. (1989). (see in particular Screening By Hybridization 1.90 and Sequencing Denatured Double-Stranded DNA Templates 13.70). Illustrative of the invention, the polynucleotide set out in Table 1 [SEQ ID NO:1] was discovered in a DNA library derived from *Streptococcus pneumoniae* 0100993.

The DNA sequence set out in Table 1 [ SEQ ID NO:1] contains an open reading frame encoding a protein having about the number of amino acid residues set forth in Table 1 [SEQ ID NO:2 or SEQ ID NO:3] with a deduced molecular weight that can be calculated using amino acid residue molecular weight values well known in the art. The polynucleotide of SEQ ID NO:1, between nucleotide number 1441 through number 3102 encodes the polypeptide of SEQ ID NO:2 and between 1414 through number 3102 encodes the polypeptide of SEQ ID NO:3. The stop codon begins at nucleotide number 3103 of SEQ ID NO:1.

The histidine kinase of the invention is structurally related to other proteins of the histidine kinase family, as shown by the results of sequencing the DNA encoding histidine kinase of the deposited strain. The protein exhibits greatest homology to YEHU from Escherichia coli protein among known proteins. Histidine kinase of Table 1 [SEQ ID NO:2 or SEQ ID NO:3] has about 23% identity over its entire length and about 48% similarity over its entire length with the amino acid sequence of YEHU from *Escherichia coli* polypeptide.

The invention provides a polynucleotide sequence identical over its entire length to the coding sequence in Table 1 [SEQ ID NO:1]. Also provided by the invention is the coding sequence for the mature polypeptide or a fragment thereof, by itself as well as the coding sequence for the mature polypeptide or a fragment in reading frame with other coding sequence, such as those encoding a leader or secretory sequence, a pre-, or pro- or prepro- protein sequence. The polynucleotide may also contain noncoding sequences, including for example, but not limited to non-oding 5' and 3' sequences, such as the transcribed, non-translated sequences, termination signals, ribosome binding sites, sequences that stabilize mRNA, introns, polyadenylation signals, and additional coding sequence which encode additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., *Proc. Natl. Acad. Sci., USA* 86: 821–824 (1989), or an HA tag (Wilson et al, *Cell* 37.: 767 (1984). Polynucleotides of the invention also include, but are not limited to, polynucleotides comprising a structural gene and its naturally associated sequences that control gene expression.

A preferred embodiment of the invention is the polynucleotide of comprising nucleotide 1441 to 3102 or nucleotide 1414 to 3102 set forth in SEQ ID NO:1 of Table 1 which encodes the histidine kinase polypeptide.

The invention also includes polynucleotides of the formula set forth in Table 1 (C) wherein, at the 5' end of the molecule, X is hydrogen, and at the 3' end of the molecule, Y is hydrogen or a metal, $R_1$ and $R_2$ is any nucleic acid residue, and n is an integer between 1 and 1000. Any stretch of nucleic acid residues denoted by either R group, where R is greater than 1, may be either a heteropolymer or a homopolymer, preferably a heteropolymer.

The term "polynucleotide encoding a polypepfide" as used herein encompasses polynucleotides that include a sequence encoding a polypeptide of the invention, particularly a bacterial polypeptide and more particularly a polypeptide of the *Streptococcus pneumoniae* histidine kinase having the amino acid sequence set out in Table 1 [SEQ ID NO:2 or SEQ ID N03]. The term also encompasses polynucleotides that include a single continuous region or discontinuous regions encoding the polypeptide (for example, interrupted by integrated phage or an insertion sequence or editing) together with additional regions, that also may contain coding and/or non-coding sequences.

The invention further relates to variants of the polynucleotides described herein that encode for variants of the polypeptide having the deduced amino acid sequence of Table 1 [SEQ ID NO:2 or SEQ ID NO3]. Variants that are fragments of the polynucleotides of the invention may be used to synthesize full-length polynucleotides of the invention.

Further particularly preferred embodiments are polynucleotides encoding histidine kinase variants, that have the amino acid sequence of histidine kinase polypeptide of Table 1 [SEQ ID NO:2 or SEQ ID NO:3] in which several, a few, 5 to 10, 1 to 5, 1 to 3, 2, 1 or no amino acid residues are substituted, deleted or added, in any combination. Especially preferred among these are silent substitutions, additions and deletions, that do not alter the properties and activities of histidine kinase.

Further preferred embodiments of the invention are polynucleotides that are at least 70% identical over their entire length to a polynucleotide encoding histidine kinase polypeptide having the amino acid sequence set out in Table 1 [SEQ ID NO:2 or SEQID NO:3], and polynucleotides that are complementary to such polynucleotides. Alternatively, most highly preferred are polynucleotides that comprise a region that is at least 80% identical over its entire length to a polynucleotide encoding histidine kinase polypeptide of the deposited strain and polynucleotides complementary thereto. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments are polynucleotides that encode polypeptides that retain substantially the same biological function or activity as the mature polypeptide encoded by the DNA of Table 1 [SEQ ID NO:1].

The invention further relates to polynucleotides that hybridize to the herein above-described sequences. In this regard, the invention especially relates to polynucleotides that hybridize under stringent conditions to the herein above-described polynucleotides. As herein used, the terms "stringent conditions" and "stringent hybridization conditions" mean hybridization will occur only if there is at least 95% and preferably at least 97% identity between the sequences. An example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 micrograms/ml denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein.

The invention also provides a polynucleotide consisting essentially of a polynucleotide sequence obtainable by screening an appropriate library containing the complete gene for a polynucleotide sequence set forth in SEQ ID NO:1 under stringent hybridization conditions with a probe having the sequence of said polynucleotide sequence set forth in SEQ ID NO:1 or a fragment thereof; and isolating said DNA sequence. Fragments useful for obtaining such a polynucleotide include, for example, probes and primers described elsewhere herein.

As discussed additionally herein regarding polynucleotide assays of the invention, for instance, polynucleotides of the invention as discussed above, may be used as a hybridization probe for RNA, CDNA and genomic DNA to isolate full-length cDNAs and genomic clones encoding histidine kinase and to isolate cDNA and genomic clones of other genes that have a high sequence similarity to the histidine kinase gene. Such probes generally will comprise at least 15 bases. Preferably, such probes will have at least 30 bases and may have at least 50 bases. Particularly preferred probes will have at least 30 bases and will have 50 bases or less.

For example, the coding region of the histidine kinase gene may be isolated by screening using the DNA sequence provided in SEQ ID NO:1 to synthesize an oligonucleotide probe. A labeled oligonucleotide having a sequence complementary to that of a gene of the invention is then used to screen a library of cDNA, genonic DNA or mRNA to determine which members of the library the probe hybridizes to.

The polynucleotides and polypeptides of the invention may be employed, for example, as research reagents and materials for discovery of treatments of and diagnostics for disease, particularly human disease, as further discussed herein relating to polynucleotide assays.

Polynucleotides of the invention that are oligonucleotides derived from the sequences of NOS: 1 and/or 2/3 may be used in the processes herein as described, but preferably for PCR, to determine whether or not the polynucleotides identified herein in whole or in part are transcribed in bacteria in infected tissue. It is recognized that such sequences will also have utility in diagnosis of the stage of infection and type of infection the pathogen has attained.

The invention also provides polynucleotides that may encode a polypeptide that is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may falcilitate manipulation of a protein for assay or production, among other things. As generally is the case in vivo, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the invention may encode a mature protein, a mature protein plus a leader sequence (which may be referred to as a preprotein), a precursor of a mature protein having one or more prosequences that are not the leader sequences of a preprotein, or a preproprotein, which is a precursor to a proprotein, having a leader sequence and one or more prosequences, which generally are removed during processing steps that produce active and mature forms of the polypeptide.

Vectors, Host Cells, Expression

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention.

For recombinant production, host cells can be genetically engineered to incorporate expression systems or portions thereof or polynucleotides of the invention. Introduction of a polynucleotide into the host cell can be effected by methods described in many standard laboratory manuals, such as Davis et al, *BASIC METHODS IN MOLECULAR BIOLOGY*, (1986) and Sambrook et al., *MOLECULAR CLONING: A LABORATORY MANUAL*, 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as streptococci, staphylococci, enterococci *E coli*, streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

A great variety of expression systems can be used to produce the polypeptides of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., *MOLECULAR CLONING, A LABORATORY MANUAL*, (supra).

For secretion of the translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. Most preferably, high performance liquid chromatography is employed for purification. Well known techniques for refolding protein may be employed to regenerate active conformation when the polypeptide is denatured during isolation and or purification.

Diagnostic Assays

This invention is also related to the use of the histidine kinase polynucleotides of the invention for use as diagnostic reagents. Detection of histidine kinase in a eukaryote, particularly a mammal, and especially a human, will provide a diagnostic method for diagnosis of a disease. Eukaryotes (herein also "individual(s)"), particularly mammals, and especially humans, infected with an organism comprising the histidine kinase gene may be de at the nucleic acid level by a variety of techniques.

Nucleic acids for diagnosis may be obtained from an infected individual's cells and tissues, such as bone, blood, muscle, cartilage, and skin. Genomic DNA may be used directly for detection or may be amplified enzymatically by using PCR or other amplification technique prior to analysis. RNA or cDNA may also be used in the same ways. Using amplification, characterization of the species and strain of prokaryote present m an individual, may be made by an analysis of the genotppe of the prokaryote gene. Deletions and insertions can be detected by a change in size of the amplified product in comparison to the genotype of a reference sequence. Point mutations can be identified by hybridizing amplified DNA to labeled histidine kinase polynucleotide sequences. Perfectly matched sequences can be distinguished from mismatched duplexes by RNase digestion or by differences in melting temperatures. DNA sequence differences may also be detected by alterations in the electrophoretic mobility of the DNA fragments in gels, with or without denaturing agents, or by direct DNA sequencing. See, e.g, Myers et al., *Science*, 230: 1242 (1985). Sequence changes at specific locations also may be revealed by nuclease protection assays, such as RNase and S1 protection or a chemical cleavage method. See, e.g., Cotton et al., *Proc. Natl. Acad. Sci., USA*, 85: 4397–4401 (1985).

Cells carrying mutations or polymorphisms in the gene of the invention may also be detected at the DNA level by a variety of techniques, to allow for serotyping, for example. For example, RT-PCR can be used to detect mutations. It is particularly preferred to used RT-PCR in conjunction with automated detection systems, such as, for example, GeneScan. RNA or cDNA may also be used for the same purpose, PCR or RT-PCR. As an example, PCR primers complementary to a nucleic acid encoding histidine kinase can be used to identify and analyze mutations. Examples of representative primers are shown below in Table 2.

TABLE 2

Primers for amplification of histidine kinase polynucleotides

| SEQ ID NO | PRIMER SEQUENCE |
|---|---|
| 6 | 5'-ATGGTTATTTCCATCTTTCTGGTC-3' |
| 7 | 5'-TCTAGTTTCTACTGTATTTATATAT-3' |

The invention further provides these primers with 1, 2, 3 or 4 nucleotides removed from the 5' and/or the 3' end. These primers may be used for, among other things, amplifying histidine kinase DNA isolated from a sample derived from an individual. The primers may be used to amplify the gene isolated from an infected individual such that the gene may then be subject to various techniques for elucidation of the DNA sequence. In this way, mutations in the DNA sequence may be detected and used to diagnose infection and to serotype and/or classify the infectious agent.

The invention further provides a process for diagnosing, disease, preferably bacterial infections, more preferably infections by *Streptococcus pneumoniae*, and most preferably otitis media, conjunctivitis, pneumonia, bacteremia, meningitis, sinusitis, pleural empyema and endocarditis, and most particularly meningitis, such as for example infection of cerebrospinal fluid, comprising determining from a sample derived from an individual a increased level of expression of polynucleotide having the sequence of Table 1 [SEQ ID NO:1]. Increased or decreased expression of histidine kinase polynucleotide can be measured using any on of the methods well known in the art for the quantation of polynucleotides, such as, for example, amplification, PCR, RT-PCR, RNase protection, Northern blotting and other hybridization methods.

In addition, a diagnostic assay in accordance with the invention for detecting over-expression of histidine kinase protein compared to normal control tissue samples may be used to detect the presence of an infection, for example. Assay techniques that can be used to determine levels of a histidine linase protein, in a sample derived from a host are well-known to those of skill in the art. Such assay methods include radioirmunoassays, competitive-binding assays, Western Blot analysis and ELISA assays.

Antibodies

The polypeptides of the invention or variants thereof, or cells expressing them can be used as an immunogen to produce antibodies immunospecific for such polypeptides. "Antibodies" as used herein includes monoclonal and polyclonal antibodies, chimeric, single chain, simianized antibodies and humanized antibodies, as well as Fab fragments, including the products of an Fab immunolglobulin expression library.

Antibodies generated against the polypeptides of the invention can be obtained by administering the polypeptides or epitope-bearing fragments, analogues or cells to an animal, preferably a nonhuman, using routine protocols. For preparation of monoclonal antibodies, any technique known in the art that provides antibodies produced by continuous cell line cultures can be used. Examples include various techniques, such as those in Kohler, G. and Milstein, C., *Nature* 256: 495–497 (1975); Kozbor et al., *Immunology Today* 4: 72 (1983); Cole et al., pg. 77–96 in MONOCLONAL ANTIBODIES AND CANCER THERAPY, Alan R. Liss, Inc. (1985).

Techniques for the production of single chain antibodies (U.S. Pat. No. 4,946,778) can be adapted to produce single chain antibodies to polypeptides of this invention. Also, transgenic mice, or other organisms such as other mammals, may be used to express humanized antibodies.

Alternatively phage display technology may be utilized to select antibody genes with binding activities towards the polypeptide either from repertoires of PCR amplified v-genes of lymphocytes from humans screened for possessing anti-histidine kinase or from naive libraries (McCafferty, J. et al., (1990), *Nature* 348, 552–554; Marks, J. et al., (1992) *Biotechnology* 10, 779–783). The affinity of these antibodies can also be improved by chain shuffling (Clackson, T. et al., (1991) *Nature* 352, 624–628).

If two antigen binding domains are present each domain may be directed against a different epitope—termed 'bispecific' antibodies.

The above-described antibodies may be employed to isolate or to identify clones expressing the polypeptides to purify the polypeptides by affinity chromatography.

Thus, among others, antibodies against histidine kinase-polypeptide may be employed to treat infections, particularly bacterial infections and especially otitis media, conjunctivitis, pneumonia, bacteremia, meningitis, sinusitis, pleural empyema and endocarditis, and most particularly meningitis, such as for example infection of cerebrospinal fluid.

Polypeptide variants include antigenically, epitopically or immunologically equivalent variants that form a particular aspect of this invention. The term "antigenically equivalent derivative" as used herein encompasses a polypeptide or its equivalent which will be specifically recognized by certain antibodies which, when raised to the protein or polypeptide according to the invention, interfere with the immediate physical interaction between pathogen and mammalian host. The term "immunologically equivalent derivative" as used herein encompasses a peptide or its equivalent which when used in a suitable formulation to raise antibodies in a vertebrate, the antibodies act to interfere with the immediate physical interaction between pathogen and mammalian host.

The polypeptide, such as an antigenically or immunologically equivalent derivative or a fusion protein thereof is used as an antigen to immunize a mouse or other animal such as a rat or chicken. The fusion protein may provide stability to the polypeptide. The antigen may be associated, for example by conjugation, with an immunogenic carrier protein for example bovine serum albumin (BSA) or keyhole limpet haemocyanin (KLH). Alternatively a multiple antigenic peptide comprising multiple copies of the protein or polypeptide, or an antigenically or immunologically equivalent polypeptide thereof may be sufficiently antigenic to improve immunogenicity so as to obviate the use of a carrier.

Preferably, the antibody or variant thereof is modified to make it less immunogenic in the individual. For example, if the individual is human the antibody may most preferably be "humanized"; where the complimentarity determining region(s) of the hybridoma-derived antibody has been transplanted into a human monoclonal antibody, for example as described in Jones, P. et al. (1986), *Nature* 321, 522–525 or Tempest et al.,(1991) *Biotechnology* 9, 266–273.

The use of a polynucleotide of the invention in genetic immunization will preferably employ a suitable delivery method such as direct injection of plasmid DNA into muscles (Wolff et al., *Hum Mol Genet* 1992, 1:363, Manthorpe et al., *Hum. Gene Ther*. 1963:4, 419), delivery of DNA complexed with specific protein carriers (Wu et al., *J Biol Chem*. 1989: 264,16985), coprecipitation of DNA with calcium phosphate (Benvenisty & Reshef, *PNAS USA*, 1986:83,9551), encapsulation of DNA in various forms of liposomes (Kaneda et al., *Science* 1989:243,375), particle bombardment (Tang et al., *Nature* 1992, 356:152, Eisenbraun et al., *DNA Cell Biol* 1993, 12:791) and in vivo infection using cloned retroviral vectors (Seeger et al., *PNAS USA* 1984:81,5849).

Antagonists and Agonists—Assays and Molecules

Polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See, e.g, Coligan et al., *Current Protocols in Immunology* 1 (2): Chapter 5 (1991).

The invention also provides a method of screening compounds to identify those which enhance (agonist) or block (antagonist) the action of histidine kinase polypeptides or polynucleotides, particularly those compounds that are bacteriostatic and/or bacteriocidal. The method of screening may involve high-throughput techniques. For example, to screen for agonists or antagoists, a synthetic reaction mix, a cellular compartment, such as a membrane, cell envelope or cell wall, or a preparation of any thereof, comprising histidine kinase polypeptide and a labeled substrate or ligand of such polypeptide is incubated in the absence or the presence of a candidate molecule that may be a histidine kinase agonist or antagonist. The ability of the candidate molecule to agonize or antagonize the histidine kinase polypeptide is reflected in decreased binding of the labeled ligand or decreased production of product from such substrate. Molecules that bind gratuitously, i.e., without inducing the effects of histidine kinase polypeptide are most likely to be good antagonists. Molecules that bind well and increase the rate of product production from substrate are agonists. Detection of the rate or level of production of product from substrate may be enhanced by using a reporter system. Reporter systems that may be usefull in this regard include but are not limted to colorimetric labeled substrate converted into product, a reporter gene that is responsive to changes in histidine kinase polynucleotide or polypeptide activity, and binding assays known in the art.

Another example of an assay for histidine kinase antagonists is a competitive assay that combines histidine kinase and a potential antagonist with histidine kinase-binding molecules, recombinant histidine kinase binding molecules, natural substrates or ligands, or substrate or ligand mimetics, under appropriate conditions for a competitive inhibition assay. Histidine kinase can be labeled, such as by radioactivity or a colorimetric compound, such that the number of histidine kinase molecules bound to a binding molecule or converted to product can be determined accurately to assess the effectiveness of the potential antagonist.

Potential antagonists include small organic molecules, peptides, polypeptides and antibodies that bind to a polynucleotide or polypeptide of the invention and thereby inhibit or extinguish its activity. Potential antagonists also may be small organic molecules, a peptide, a polypeptide such as a closely related protein or antibody that binds the same sites on a binding molecule, such as a binding molecule, without inducing histidine kinase-induced activities, thereby preventing the action of histidine kinase by excluding histidine kinase from binding.

Potential antagonists include a small molecule that binds to and occupies the binding site of the polypeptide thereby preventing binding to cellular binding molecules, such that normal biological activity is prevented. Examples of small molecules include but are not limited to small organic molecules, peptides or peptide-like molecules. Other potential antagonists include antisense molecules (see Okano, *J Neurochem*. 56. 560 (1991); *OLIGODEOXYNUCLEOTIDES AS ANTISENSE INHIBITORS OF GENIE EXPRESSION*, CRC Press, Boca Raton, Fla. (1988), for a description of these molecules). Preferred potential antagonists include compounds related to and variants of histidine kinase.

Each of the DNA sequences provided herein may be used in the discovery and development of antibacterial compounds. The encoded protein, upon expression, can be used as a target for the screening of antibacterial drugs. Additionally, the DNA sequences encoding the amino terminal regions of the encoded protein or Shine-Delgarno or other translation facilitating sequences of the respective mRNA can be used to construct antisense sequences to control the expression of the coding sequence of interest.

The invention also provides the use of the polypeptide, polynucleotide or inhibitor of the invention to interfere with the initial physical interaction between a pathogen and mammalian host responsible for sequelae of infection. In particular the molecules of the invention may be used: in the prevention of adhesion of bacteria, in particular gram positive bacteria, to mammalian extracellular matrix proteins on in-dwelling devices or to extracellular matrix proteins in wounds; to block histidine kinase protein-mediated mammalian cell invasion by, for example, initiating phosphorylation of mammalian tyrosine kinases (Rosenshine et al., Infect. Immun. 60:2211 (1992); to block bacterial adhesion between mammalian extracellular matrix proteins and bacterial histidine kinase proteins that mediate tissue damage and; to block the normal progression of pathogenesis in infections initiated other than by the implantation of in-dwelling devices or by other surgical techniques.

This invention provides a method of screening drugs to identify those which interfere with i) the interaction of the histidine kinase with a response regulator, the method comprising incubating the histidine kinase with response regulator in the presence of the drug and measuring the ability of the drug to block this interaction; and/or ii) the ability of the histidine kinase to autophosphorylate, the method comprising incubating the histidine kinase with the drug and measuring the ability of the drug to prevent autophosphorylation.

The response regulator is preferably the cognate response regulator of the histidine kinase, or another response regulator which is capable of using the histidine kinase as a substrate, and is preferably from *Streptococcus pneumoniae* or another microorganism e.g. Bacillus. Polypeptide and polynucleotide sequences of the cognate response regulator of the Histidine kinase of the invention are set forth in Table 1 (G and H). This novel response regulator shows 25% identity to the DegU response regulator protein from *Bacillus brevis*.

The antagonists and agonists of the invention may be employed, for instance, to inhibit and treat otitis media, conjunctivitis, pneumonia, bacteremia, meningitis, sinusitis, pleural empyema and endocarditis, and most particularly meningitis, such as for example infection of cerebrospinal fluid.

Vaccines

Another aspect of the invention relates to a method for inducing an immunological response in an individual, particularly a mammal which comprises inoculating the individual with histidine kinase, or a fragment or variant thereof, adequate to produce antibody and/ or T cell immune response to protect said individual from infection, particularly bacterial infection and most particularly *Streptococcus pneumoniae* infection. Also provided are methods whereby such immunological response slows bacterial replication. Yet another aspect of the invention relates to a method of inducing immunological response in an individual which comprises delivering to such individual a nucleic acid vector to direct expression of histidine kinase, or a fragment or a variant thereof, for expressing histidine kinase, or a fragment or a variant thereof in vivo in order to induce an immunological response, such as, to produce antibody and/ or T cell immune response, including, for example, cytokine-producing T cells or cytotoxic T cells, to protect said individual from disease, whether that disease is already established within the individual or not. One way of administering the gene is by accelerating it into the desired cells as a coating on particles or otherwise. Such nucleic acid vector may comprise DNA, RNA, a modified nucleic acid, or a DNA/RNA hybrid.

A further aspect of the invention relates to an immunological composition which, when introduced into an individual capable or having induced within it an immunological response, induces an immunological response in such individual to a histidine kinase or protein coded therefrom, wherein the composition comprises a recombinant histidine kinase or protein coded therefrom comprising DNA which codes for and expresses an antigen of said histidine kinase or protein coded therefrom. The immunological response may be used therapeutically or prophylactically and may take the form of antibody immunity or cellular immunity such as that arising from CTL or CD4+T cells.

A histidine kinase polypeptide or a fragment thereof may be fused with co-protein which may not by itself produce antibodies, but is capable of stabilizing the first protein and producing a fused protein which will have immunogenic and protective properties. Thus fused recombinant protein, preferably further comprises an antigenic co-protein, such as lipoprotein D from *Hemophilus influenzae*, Glutathione-S-transferase (GST) or beta-galactosidase, relatively large co-proteins which solubilize the protein and facilitate production and purification thereof. Moreover, the co-protein may act as an adjuvant in the sense of providing a generalized stimulation of the immune system. The co-protein may be attached to either the amino or carboxy terminus of the first protein.

Provided by this invention are compositions, particularly vaccine compositions, and methods comprising the polypeptides or polynucleotides of the invention and immunostimulatory DNA sequences, such as those described in Sato, Y. et al. *Science* 273: 352 (1996).

Also, provided by this invention are methods using the described polynucleotide or particular fragments thereof which have been shown to encode non-variable regions of bacterial cell surface proteins in DNA constructs used in such genetic immunization experiments in animal models of infection with *Streptococcus pneumoniae* will be particularly useful for identifying protein epitopes able to provoke a prophylactic or therapeutic immune response. It is believed that this approach will allow for the subsequent preparation of monoclonal antibodies of particular value from the requisite organ of the animal successfully resisting or clearing infection for the development of prophylactic agents or therapeutic treatments of bacterial infection, particularly *Streptococcus pneumoniae* infection, in mammals, particularly humans.

The polypeptide may be used as an antigen for vaccination of a host to produce specific antibodies which protect against invasion of bacteria, for example by blocking adherence of bacteria to damaged tissue. Examples of tissue damage include wounds in skin or connective tissue caused, e.g., by mechanical, chemical or thermal damage or by implantation of indwelling devices, or wounds in the mucous membranes, such as the mouth, mammary glands, urethra or vagina.

The invention also includes a vaccine formulation which comprises an immunogenic recombinant protein of the invention together with a suitable carrier. Since the protein may be broken down in the stomach, it is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteriostats and solutes which render the formulation insotonic with the bodily fluid, preferably the blood, of the individual; and aqueous and non-aqueous sterile suspensions which may include suspending agents or thickening agents. The formulations may be presented in unit-dose or multi-dose containers, for example, sealed ampules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

While the invention has been described with reference to certain histidine kinase protein, it is to be understood that this covers fragments of the naturally occurring protein and similar proteins with additions, deletions or substitutions which do not substantially affect the immunogenic properties of the recombinant protein.

Compositions, Kits and Administration

The invention also relates to compositions comprising the polynucleotide or the polypeptides discussed above or their agonists or antagonists. The polypeptides of the invention may be employed in combination with a non-sterile or sterile carrier or carriers for use with cells, tissues or organisms, such as a phannaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration. The invention further relates to diagnostic and pharmaceutical packs and kits comprising one or more containers filled with one or more of the ingredients of the aforementioned compositions of the invention.

Polypeptides and other compounds of the invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

In therapy or as a prophylactic, the active agent may be administered to an individual as an injectable composition, for example as a sterile aqueous dispersion, preferably isotonic.

Alternatively the composition may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

In-dwelling devices include surgical implants, prosthetic devices and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, continuous ambulatory peritoneal dialysis (CAPD) catheters.

The composition of the invention may be administered by injection to achieve a systemic effect against relevant bacteria shortly before insertion of an in-dwelling device. Treatment may be continued after surgery during the in-body time of the device. In addition, the composition could also be used to broaden perioperative cover for any surgical technique to prevent bacterial wound infections, especially *Streptococcus pneumoniae* wound infections.

Many orthopaedic surgeons consider that humans with prosthetic joints should be considered for antibiotic prophylaxis before dental treatment that could produce a bacteremia. Late deep infection is a serious complication sometimes leading to loss of the prosthetic joint and is accompanied by significant morbidity and mortality. It may therefore be possible to extend the use of the active agent as a replacement for prophylactic antibiotics in this situation.

In addition to the therapy described above, the compositions of this invention may be used generally as a wound treatment agent to prevent adhesion of bacteria to matrix proteins exposed in wound tissue and for prophylactic use in dental treatment as an alternative to, or in conjunction with, antibiotic prophylaxis.

Alternatively, the composition of the invention may be used to bathe an indwelling device immediately before insertion. The active agent will preferably be present at a concentration of 14 μg/l to 10 mg/ml for bathing of wounds or indwelling devices.

A vaccine composition is conveniently in injectable form. Conventional adjuvants may be employed to enhance the immune response. A suitable unit dose for vaccination is 0.5–5 microgram/kg of antigen, and such dose is preferably administered 1–3 times and with an interval of 1–3 weeks. With the indicated dose range, no adverse toxicological effects will be observed with the compounds of the invention which would preclude their administration to suitable individuals.

Each reference disclosed herein is incorporated by reference herein in its entirety. Any patent application to which this application claims priority is also incorporated by reference herein in its entirety.

EXAMPLES

The examples below are carried out using standard techniques, which are well known and routine to those of skill in the art, except where otherwise described in detail. The examples are illustrative, but do not limit the invention.

Example 1

Strain Selection, Library Production and Sequencing

The polynucleotide having the DNA sequence given in SEQ ID NO:1 was obtained from a library of clones of chromosomal DNA of *Streptococcus pneumoniae* in *E. coli*. The sequencing data from two or more clones containing overlapping *Streptococcus pneumoniae* DNAs was used to construct the contiguous DNA sequence in SEQ ID NO:1. Libraries may be prepared by routine methods, for example: Methods 1 and 2 below.

Total cellular DNA is isolated from *Streptococcus pneumoniae* 0100993 according to standard procedures and size-fractionated by either of two methods.

Method 1

Total cellular DNA is mechanically sheared by passage through a needle in order to size-fractionate according to standard procedures. DNA fragments of up to 11 kbp in size are rendered blunt by treatment with exonuclease and DNA polymerase, and EcoRI linkers added. Fragments are ligated into the vector Lambda ZapII that has been cut with EcoRI, the library packaged by standard procedures and *E.coli* infected with the packaged library. The library is amplified by standard procedures.

Method 2

Total cellular DNA is partially hydrolyzed with a one or a combination of restriction enzymes appropriate to generate a series of fragments for cloning into library vectors (e.g., RsaI, PalI, AluI, Bshl235I), and such fragments are size-fractionated according to standard procedures. EcoRI linkers are ligated to the DNA and the fragments then ligated into the vector Lambda ZapII that have been cut with EcoRI, the library packaged by standard procedures, and *E.coli* infected with the packaged library. The library is amplified by standard procedures.

What is claimed is:

1. An isolated polynucleotide segment comprising a nucleic acid sequence that encodes a polypeptide comprising the amino acid sequence of SEQ ID NO:3, wherein the nucleic acid sequence is not genomic DNA.

2. A vector comprising the isolated polynucleotide segment of claim 1.

3. An isolated host cell comprising the vector of claim 2.

4. A process for producing a polypeptide comprising culturing the host cell of claim 3 under conditions sufficient for the production of the polypeptide, wherein the polypeptide comprises SEQ ID NO:3.

5. An isolated polynucleotide segment comprising nucleotides 1414 to 3102 set forth in SEQ ID NO:1.

6. A vector comprising the isolated polynucleotide segment of claim 5.

7. An isolated host cell comprising the vetor of claim 6.

8. A process for producing a polypeptide comprising culturing the host cell of claim 7 under conditions sufficient for life production of the polypeptide, wherein the polypeptide comprises SEQ ID NO:3.

9. An isolated polynucleotide comprising a nuclei acid sequence which encodes a polypeptide consisting of the amino acid sequence of SEQ ID NO:3, wherein the nucleic acid sequence is not genomic DNA.

10. A vector comprising the isolated polynucleotide of claim 9.

11. An isolated host cell comprising the vector of claim 10.

12. A process for producing a polypeptide comprising culturing the host cell of claim 11 under conditions sufficient for the production of the polypeptide, wherein the polypeptide consists of SEQ ID NO:3.

13. An isolated polynucleotide segment comprising the full complement of the nucleotide sequence of claim 1, wherein the full complement is not genomic DNA and wherein the full complement detects *Streptococcus pneumoniae* by hybridization.

14. An isolated polynucleotide segement comprising the full complement of the nucleotide sequence of claim 9, wherein the full conplenent is not genomic DNA and wherein the full complement detects *streptococcus pneumoniae* by hybridazation.

* * * * *